US007923428B2

(12) United States Patent
Geffroy et al.

(10) Patent No.: US 7,923,428 B2
(45) Date of Patent: Apr. 12, 2011

(54) COMPOSITION FOR CLEANING OR RINSING HARD SURFACES

(75) Inventors: Cédric Geffroy, Poitiers (FR); Ian Harrison, Poissy (FR); Marie-Pierre Labeau, Paris (FR)

(73) Assignee: Rhodia Chimie, Aubervilliers (FR)

( * ) Notice: Subject to any disclaimer, the term of this patent is extended or adjusted under 35 U.S.C. 154(b) by 746 days.

(21) Appl. No.: 10/546,768

(22) PCT Filed: Dec. 19, 2003

(86) PCT No.: PCT/FR03/03841

§ 371 (c)(1), (2), (4) Date: Apr. 18, 2006

(87) PCT Pub. No.: WO2004/083354

PCT Pub. Date: Sep. 30, 2004

(65) Prior Publication Data

US 2006/0217286 A1 Sep. 28, 2006

(30) Foreign Application Priority Data

Feb. 20, 2003 (FR) ..................................... 03 02079
Aug. 1, 2003 (FR) ..................................... 03 09527

(51) Int. Cl.
*C07C 323/25* (2006.01)
*C11D 1/10* (2006.01)

(52) U.S. Cl. ........ 510/492; 510/490; 510/504; 510/382; 510/235; 510/220; 510/109; 510/495

(58) Field of Classification Search .................... 510/49, 510/492, 504, 382, 235, 220, 109, 490
See application file for complete search history.

(56) References Cited

U.S. PATENT DOCUMENTS 3,478,001 A * 11/1969 Bahr et al. .................... 526/265
3,520,818 A * 7/1970 Cambre ........................ 510/398
3,549,605 A * 12/1970 Whiteley et al. .............. 526/287
3,671,305 A * 6/1972 Brown ............................ 442/93
3,671,502 A * 6/1972 Samour et al. ................ 526/287
4,287,080 A 9/1981 Siklosi
4,470,923 A 9/1984 Koster
4,557,853 A 12/1985 Collins
4,607,076 A * 8/1986 Schulz et al. ................. 524/548
4,742,135 A * 5/1988 Schulz et al. ................. 526/265
4,882,405 A * 11/1989 Schulz et al. ................. 526/265
5,108,660 A 4/1992 Michael
5,114,606 A 5/1992 Van Vliet et al.
5,280,117 A 1/1994 Kerschner et al.
5,476,660 A * 12/1995 Somasundaran et al. ..... 424/401
5,536,452 A 7/1996 Black
5,559,261 A 9/1996 Sivik
5,587,022 A 12/1996 Black
5,710,119 A * 1/1998 Busch et al. .................. 510/360
5,863,880 A * 1/1999 Shih et al. ...................... 510/361
6,191,098 B1 * 2/2001 Rodrigues et al. ............ 510/475
6,391,995 B2 * 5/2002 Murugan et al. .............. 526/265
6,569,261 B1 5/2003 Aubay et al.
7,544,649 B2 * 6/2009 Aihara et al. ................. 510/191
2002/0090349 A1 * 7/2002 Bergeron et al. .......... 424/70.11
2008/0312118 A1 * 12/2008 Futterer et al. ................ 510/180
2010/0004152 A1 * 1/2010 Karagianni et al. .......... 510/180
2010/0056415 A1 * 3/2010 Rong et al. ..................... 510/238
2010/0273697 A1 * 10/2010 Vuong et al. .................. 510/220

FOREIGN PATENT DOCUMENTS

EP 0 112 592 A2 * 7/1984
EP 0 488 868 6/1992
EP 0 810 239 7/1992
EP 0 561 656 9/1993
EP 0 909 809 11/2004
EP 1 196 527 2/2005
EP 1 196 528 8/2010
FR 2 796 390 1/2001
FR 2 796 391 1/2001
FR 2 813 312 3/2002
JP 59-073560 4/1984
JP 11-349826 6/2001
JP 2002-069178 3/2002
WO WO 96/23859 8/1996
WO WO 96/23860 8/1996
WO WO 96/23861 8/1996

OTHER PUBLICATIONS

Gauthier et al., Journal of Polymer Science, vol. 40, pp. 511-523 (2002).
Lee and Chan-Chan Tsai, Polymer, vol. 35, No. 10, pp. 2210-2217 (1994).
Soto et al., Polymer, vol. 25, pp. 121-128 (1984).
Koberle et al., Macromolecules, vol. 27, pp. 2165-2173 (1994).
Castano et al., Journal of Materials Research, vol. 5, No. 3, pp. 654-657 (1990).
Favresse et al., Macromolecular Chemistry and Physics, vol. 200, No. 4, pp. 887-895 (1999).
Pujol-Fortin et al., Maromolecules, vol. 24, No. 16, pp. 4523-4530 (1991).
Berlinova et al., Polymer, vol. 41, pp. 831-837 (2000).
Lee et al., Polymer, vol. 38, No. 4, pp. 971-979 (1997).
Lee et al., Journal of Applied Polymer Science, vol. 80, pp. 1619-1626 (2001).
Lowe et al., Chemical Communications, pp. 1555-1556 (1996).
Lowe, Macromolecules, vol. 32, pp. 2141-2146 (1999).
Hamaide, Macromolecular Chemistry, vol. 187, pp. 1097-1107 (1986).
International Search Report for International Application No. PCT/FR2003/03841 mailed Jun. 23, 2004.

* cited by examiner

*Primary Examiner* — Mark Eashoo
*Assistant Examiner* — Jane L Stanley
(74) *Attorney, Agent, or Firm* — Hunton & Williams LLP

(57) ABSTRACT

Composition for cleaning or rinsing hard surfaces in an aqueous or aqueous/alcoholic medium comprising at least one polybetaine for contributing to said surfaces antideposition and/or antiadhesion properties with regard to soiling substances capable of being deposited on said surface.

28 Claims, No Drawings

COMPOSITION FOR CLEANING OR RINSING HARD SURFACES

This application is an application under 35 U.S.C. Section 371 of International Application Number PCT/FR2003/003841 filed on Dec. 19, 2003.

A subject matter of the present invention is a cleaning or rinsing composition intended for the treatment of industrial, domestic or communal hard surfaces, in particular of ceramic, tiling, window, metal, melamine, formica or plastic type, targeted at conferring on the latter in particular persistent antideposition and/or antiadhesion properties with regard to soiling substances; in addition, it can contribute antistatic, gloss or slip-resistance properties to the latter.

A subject matter of the invention is more particularly a cleaning or rinsing composition intended for the treatment of a hard surface, which composition is capable of conferring, on the latter, persistent antideposition and/or antiadhesion properties with regard to soiling substances, so as to prevent the subsequent presence of marks due in particular:

- to the drying of drops of water deposited on said surface (for example deposit of inorganic salts)
- to the attachment of inorganic or organic particles present in the surrounding air (case of the cleaning of skyscrapers) or deposited by contact (case of the cleaning of floors, toilets, and the like)
- to the deposition by spattering of fatty organic compounds (cooking fats)
- to the deposition of soaps and their metal salts
- to the deposition of compounds of vegetable origin of hydrocolloid or polysaccharide type.

Commercial detergent formulations make it possible to efficiently clean industrial, domestic or communal hard surfaces. They are generally composed of an aqueous solution of surfactants, in particular of nonionic and anionic or nonionic and cationic surfactants, of solvents, of alcohol(s), in order to facilitate drying, and optionally of sequestering agents and of bases or acids, in order to adjust the pH. A frequent disadvantage of these detergent formulations is that the subsequent contact of the hard surface with water results, during drying, in the formation of marks. In addition, the treatment with these formulations is only, for the majority of them, purely curative and not preventative. Thus, industrial or domestic cleaners are effective in cleaning the soiled hard surface but do not make it possible to prevent or limit the future fouling thereof or even to promote the subsequent cleaning thereof.

A solution to this problem was provided in EP-A-1 196 527, EP-A-1 196 528 and EP-A-1 196 523 by deposition on the surface, via a cleaning or rinsing formulation, of a water-soluble, amphoteric organic copolymer derived from a cationic monomer and from an anionic or potentially anionic monomer in an amount sufficient to render the surface hydrophilic (or to improve its hydrophilicity, in order to obtain a contact angle which is as low as possible between the hard surface to be treated and a drop of water) but also to ensure the retention of water close to the hard surface thus treated.

Provision has been made to contribute permanent antistatic, soil-release and/or fungicidal properties to articles made of textile fibers (in particular cotton and polyester) by padding said articles at 130-200° C. using a bath (pad-bath solution) comprising a betaine polymer or copolymer, a thermosetting aminoplast condensate and a catalyst, drying and heat treatment at 130-200° C. (U.S. Pat. No. 3,671,305).

Provision has also been made to introduce, into detergent compositions for the washing of textile articles (laundry), zwitterionic polymers, in particular polybetaine polymers, the anionic groups of which are connected to the cationic groups via polyether chains, as additive which makes it possible to remove clayey particulate soiling substances and as antiredeposition additive (EP-B-112 592).

The Applicant Company has now found that the deposition on a hard surface, via a cleaning or rinsing formulation, of polybetaine zwitterions exhibiting one or more permanent positive charges and one or more permanent negative charges on the same monomer unit, the number of positive charges being equal to the number of negative charges on this same monomer unit, makes it possible to confer, on the surface thus treated, persistent antideposition and/or antiadhesion properties with regard to soiling substances which are particularly outstanding; in addition, the presence of polybetaine zwitterions makes it possible to improve the cleaning ability of said formulation.

The term "persistent antideposition and/or antiadhesion properties" is understood to mean that the treated surface retains these properties over time, including after subsequent contacts with a soiling substance (for example rainwater, water from the distribution network, rinsing water to which rinsing products have or have not been added, spattered fats, soaps, and the like). This property of persistence can be observed beyond approximately 10 rinsing cycles, indeed even, in some specific cases where numerous rinsings are carried out (case of toilets, for example), beyond 100 rinsing cycles.

The above expression of "conferring, on the surface thus treated, antideposition properties" means more particularly that the treated surface, brought into contact with a soiling substance in a predominantly aqueous medium, will not have a tendency to "capture" said soiling substance, which thus significantly reduces the deposition of the soiling substance on the surface.

The above expression of "conferring, on the surface thus treated, antiadhesion properties" means more particularly that the treated surface is capable of interacting only very slightly with the soiling substance which has been deposited thereon, which makes possible easy removal of the soiling substances from the soiled treated surface; this is because, during the drying of the soiling substance brought into contact with the treated surface, the bonds developed between the soiling substance and the surface are very weak; thus, to break these bonds requires less energy (thus less effort) during the cleaning operation.

When it is said that the presence of polybetaine zwitterions makes it possible "to improve the cleaning ability" of a formulation, this means that, for the same amount of cleaning formulation (in particular a formulation for washing dishes by hand), the formulation comprising polybetaine zwitterions makes it possible to clean a greater number of soiled objects than a formulation which is devoid thereof.

In addition, the deposition on a hard surface of polybetaine zwitterions makes it possible to contribute antistatic properties to this surface; this property is particularly advantageous in the case of synthetic surfaces.

The presence of polybetaine zwitterions in formulations for the treatment of a hard surface makes it possible to render the surface hydrophilic or to improve its hydrophilicity.

The property of hydrophilization of the surface makes it possible in addition to reduce the formation of condensation on the surface; this advantage can be made use of in cleaning formulations for windows and mirrors, in particular in bathrooms. Furthermore, the rate of drying of the surface, immediately after treatment thereof by the application of the polymer but also after subsequent and repeated contacts with an aqueous medium, is very significantly improved.

A first subject matter of the invention consists of a composition for the cleaning or rinsing in an aqueous or aqueous/alcoholic medium of hard surfaces comprising at least one surface-active agent and at least one polybetaine (B), said polybetaine (B) being characterized in that it:

carries, within a pH range from 1 to 14, a permanent anionic overall charge and a permanent cationic overall charge, each individual betaine unit carrying as many permanent anionic charges as permanent cationic charges, and exhibits an absolute weight-average molar mass ($M_w$) ranging from 5000 to 3 000 000 g/mol, preferably from 8000 to 1 000 000 g/mol, very particularly between 10 000 and 500 000 g/mol.

The term "hard surfaces" is to be taken in the broad sense; it refers to nontextile surfaces which can equally well be domestic, communal or industrial surfaces.

They can be made of any material, in particular of the following types:

ceramic (surfaces such as bathroom sinks, bath tubs, wall or floor tiles, toilet bowls and the like), glass (surface such as interior or exterior windows of buildings or of vehicles, or mirrors, metal (surfaces such as internal or external walls of reactors, blades, panels, pipes, and the like), synthetic resins (for example bodywork or interior surfaces of motorized vehicles (automobiles, trucks, buses, trains, planes, and the like), melamine or formica surfaces for the interior of offices, kitchens, and the like), plastics (for example poly(vinyl chloride) or polyamide, for the interior of vehicles, in particular automobiles).

The "hard surfaces" according to the invention are surfaces which are not very porous and which are non-fibrillate; they are thus to be distinguished from textile surfaces (fabrics, fitted carpets, clothes, and the like, made of natural, artificial or synthetic materials).

The composition according to the invention, capable of contributing, to the hard surfaces to be treated, antideposition and/or antiadhesion properties with regard to soiling substances, can be:

a cleaning or rinsing composition for domestic use; it can be universal or can be more specific, such as a composition for cleaning or rinsing the bathroom; said composition prevents in particular deposition of soap salts around bath tubs and on bathroom sinks, prevents the growth and/or the deposition of calcium crystals on these surfaces, and delays the appearance of subsequent soap stains;

the kitchen; said composition makes it possible to improve the cleaning of worktops when the latter are soiled by unsaturated fatty soiling substances capable of crosslinking over time; the greasy stains come off with water without rubbing;

floors (made of linoleum, tiling or cement); said composition makes it possible to improve the removal of dust or soiling substances of argilo-calcareous types (soil, sand, mud, and the like); stains on the floor can be cleaned without effort by simple sweeping, without brushing; in addition, said composition contributes slip-resistance properties;

toilet bowls; said composition makes it possible to prevent the adhesion of traces of excrement to the surface; the flow alone of the flush of water is sufficient to remove these traces; the use of a brush is unnecessary;

windows or mirrors; said composition makes it possible to prevent the deposition of inorganic or organic particulate soiling substances on the surface;

dishes, by hand or using an automatic device; said composition makes it possible, in the case of washing by hand, to facilitate the removal of the residual stains from dried foods and to wash a larger number of items of cutlery or utensils with the same volume of washing medium; the surface of the still wet items of cutlery and utensils is no longer slippery and thus does not escape from the hands of the user; a squeaky clean effect has also been observed, namely that the surface "squeaks" under the effect of rubbing with the finger. In the case of washing or rinsing in a dishwasher, said composition makes possible the antiredeposition of soiling substances originating from foodstuffs and of insoluble inorganic calcium salts, and contributes shininess to the utensils and items of cutlery; the composition also makes it possible no longer to have to "prewash" the items of cutlery or utensils before they are introduced into the dishwasher.

A cleaning or rinsing composition for industrial or communal use; it can be universal or more specific, such as a composition for cleaning reactors, steel blades, sinks or tanks, dishes, exterior or interior surfaces of buildings, windows of buildings, including apartment buildings, bottles.

The composition according to the invention can be provided in any form and can be used in multiple ways. Thus, it can be in the form of a gelled or ungelled liquid to be deposited as such, in particular by spraying, directly on the surfaces to be cleaned or rinsed, or on a sponge or another substrate (woven or nonwoven article made of cellulose, for example) before being applied to the surface to be treated, of a gelled or ungelled liquid to be diluted in water (optionally with the addition of another solvent) before being applied to the surface to be treated, of a gelled or ungelled liquid held in a water-soluble bag, of a foam, of an aerosol, of a liquid absorbed on an absorbent substrate made of an article which is woven or nonwoven in particular (wipe), of a solid, in particular a tablet, optionally held in a water-soluble bag, it being possible for said composition to represent all or part of the tablet.

For satisfactory implementation of the invention, said polybetaine (B) is present in the composition forming the subject matter of the invention in an amount which is effective in contributing, to said surfaces, antideposition and/or antiadhesion properties with regard to soiling substances capable of being deposited on said surfaces.

Said composition forming the subject matter of the invention can comprise, depending on its application, from 0.001 to 10% of its weight of at least one polybetaine (B).

The pH of the composition or the pH of use of the composition according to the invention can vary, depending on the applications and the surfaces to be treated, from 1 to 14, indeed even from 0.5 to 14. Extreme pH values are conventional in the applications of industrial or communal cleaning type. In the field of domestic applications, the pH values range instead from 1 to 13, depending on the applications.

Said composition can be employed for the cleaning or rinsing of hard surfaces in an amount such that, after optional rinsing and after drying, the amount of polybetaine (B) deposited on the surface is from 0.0001 to 10 $mg/m^2$, preferably from 0.001 to 5 $mg/m^2$, of surface treated.

Unless otherwise indicated, when molar mass is referred to, the reference will be to the weight-average molar mass, expressed in g/mol. The latter can be determined by aqueous gel permeation chromatography (GPC) or by light scattering (DLS or alternatively MALLS), with an aqueous eluent or an organic eluent (for example dimethylacetamide, dimethylformamide, and the like), depending on the composition of the polymer.

By definition, polybetaines are polymeric zwitterions carrying one or more positive charges and one or more negative charges on the same betaine monomer unit. On the same betaine monomer unit, the number of positive charge(s) is equal to the number of negative charge(s).

According to the invention, the polybetaine (B) exhibits a permanent anionic charge and a permanent cationic charge both at highly acidic pH and at highly basic pH; these charges are permanent within a pH range from 1 to 14.

The permanent anionic charge can be contributed by one or more sulfonate, phosphate, phosphonate, phosphinate or ethenolate anions, and the like.

The cationic charge can be contributed by one or more onium or inium cations of the nitrogen (ammonium, pyridinium or imidazolinium cations), phosphorus (phosphonium, and the like) or sulfur (sulfonium, and the like) family.

Preferably, the betaine functional groups of the polybetaine (B) are carried by pendent groups.

For the same betaine monomer unit, the atom carrying the permanent cationic charge is preferably connected to the anion carrying the permanent anionic charge via an optionally substituted polyvalent hydrocarbon group, in particular an alkylene group, optionally substituted by one or more hydroxyl groups. The groups carrying equal permanent positive and negative charges exhibit one or more betaine functional groups which can be represented, in the case of the cations of the nitrogen family, by the following formulae (I) to (V), exhibiting a cationic charge at the center of the functional group and an anionic charge at the end of the functional group, and the formula (VI), exhibiting an anionic charge at the center of the functional group and a cationic charge at the end of the functional group:

$$—N^{(+)}(R^1)(R^2)—R\text{-}A\text{-}O^{(-)} \quad (I)$$

$$—(R^3)C{=}N^{(+)}(R^4)—R\text{-}A\text{-}O^{(-)} \quad (II)$$

$$—(R^3)(R)C—N^{(+)}(R^4)(R^5)—R\text{-}A\text{-}O^{(-)} \quad (III)$$

$$—N^{(+)}({=}R^6)—R\text{-}A\text{-}O^{(-)} \quad (IV)$$

$$—N^{(+)}(R^1)(R^2)—R—W^{(-)} \quad (V)$$

$$—R\text{-}A'(—O^{(-)})—R—N^{(+)}(R^1)(R^2)(R^7) \quad (VI)$$

in which formulae (I) to (IV)

the symbols $R^1$, $R^2$ and $R^5$, which are alike or different, represent an alkyl radical comprising from 1 to 7 carbon atoms, preferably from 1 to 2 carbon atoms, the symbols $R^3$ and $R^4$ represent hydrocarbon radicals which form, with the nitrogen atom, a nitrogenous heterocycle optionally comprising one or more other heteroatoms, in particular nitrogen heteroatoms, the symbol $R^6$ represents a hydrocarbon radical which forms, with the nitrogen atom, a saturated or unsaturated nitrogenous heterocycle optionally comprising one or more other heteroatoms, in particular nitrogen heteroatoms, the symbol R represents a linear or branched alkylene radical comprising from 1 to 15 carbon atoms, preferably from 2 to 4 carbon atoms, which is optionally substituted by one or more hydroxyl groups, or a benzylene radical, the symbol A represents S (═O)(═O), OP (═O)(═O) OP(═O)(OR'), P(═O)(OR') or P(═O)(R'), where R' represents an alkyl radical comprising from 1 to 7 carbon atoms or a phenyl radical, in which formula (V)

the symbols $R^1$, $R^2$ and R have the definitions given above the symbol W represents an ethenolate functional group of formula $$O—C(O^{(-)}){=}C(C{\equiv}N)_2$$

$$O—C(O)—C^{(-)}(C{\equiv}N)_2$$

$$O—C(O)—C(—C{\equiv}N)({=}C{=}N^{(-)})$$

in which formula (VI)

the symbols $R^1$ and $R^2$ have the definitions given above, the symbol $R^7$, which is identical to or different from $R^1$ or $R^2$, represents an alkyl radical comprising from 1 to 7 carbon atoms, preferably from 1 to 2 carbon atoms, the symbol A' represents —O—P(═O)—O—;

in the case of cations of the phosphorus family, mention may be made of the betaine functional groups of formulae (VII) and (VIII)

$$—P^{(+)}(R^1)(R^2)—R\text{-}A\text{-}O^{(-)} \quad (VII)$$

$$—R\text{-}A'\ (—O^{(-)})—R—P^{(+)}(R^1)(R^2)(R^7) \quad (VIII)$$

in which formula (VII) the symbols $R^1$, $R^2$, R et A have the definitions given above, in which formula (VIII)

the symbols $R^1$, $R^2$, $R^7$ and R have the definitions given above, the symbol A' represents —O—P(═O)—O—;

in the case of cations of the sulfur family, mention may be made of the betaine functional groups of formulae (IX) and (X)

$$—S^{(+)}(R^1)—R\text{-}A\text{-}O^{(-)} \quad (IX)$$

$$—R\text{-}A'\ (—O^{(-)})—R—S^{(+)}(R^1)(R^2) \quad (X)$$

in which formula (IX) the symbols $R^1$, R and A have the definitions given above, in which formula (X)

the symbols $R^1$, $R^2$ and R have the definitions given above, the symbol A' represents —O—P(═O)—O—.

The betaine functional groups can be connected to the carbon atoms of the hydrocarbon chain (also known as backbone) of the polybetaine (B) in particular via a divalent or polyvalent hydrocarbon unit (for example alkylene or arylene unit) optionally interrupted by one or more heteroatoms, in particular oxygen atoms, an ester unit or an amide unit or else via a valency bond.

Preferably, the hydrocarbon chain (or backbone) of the polybetaine (B) is a (linear or branched) polyalkylene chain optionally interrupted by one or more nitrogen and/or sulfur heteroatoms.

The polybetaine (B) according to the invention can be a homopolymer formed of identical betaine units or a copolymer formed of betaine units, at least two of which are different.

Said polybetaine (B) can additionally comprise at least one unit which is nonionic or nonionogenic at the pH of the composition or at the pH of use of the composition comprising the polybetaine (B) and/or at least one unit which is anionic or potentially anionic at the pH of the composition or at the pH of use of the composition comprising the polybetaine (B). These units can be hydrophilic or hydrophobic. They can represent up to 80% by weight or more specifically up to 90 mol % of the polybetaine (B) polymer.

However, preferably, the nonionic, nonionogenic, anionic or potentially anionic units are limited in number in order for said polybetaine (B) to retain its main characteristic of zwitterion.

Preferably, the polybetaine (B) can comprise less than 50% of its weight or more specifically less than 70 mol % of nonionic, nonionogenic, anionic or potentially anionic units; very preferably, the polybetaine (B) can comprise less than 50 mol % and more particularly less than 30 mol % of nonionic, nonionogenic, anionic or potentially anionic units.

Mention may be made, among the nonionic units which can be present, of those derived from ethylenically unsaturated nonionic monomers, such as acrylamide, vinyl acetate (capable of forming vinyl alcohol units by hydrolysis), $C_1$-$C_4$ alkyl esters of acrylic acid and of methacrylic acid, $C_1$-$C_4$ hydroxyalkyl esters of acrylic acid and of methacrylic acid, in particular ethylene glycol and propylene glycol acrylate and methacrylate, polyalkoxyl esters of acrylic acid and of methacrylic acid, in particular polyethylene glycol and polypropylene glycol esters, and the like.

Mention may be made, among the units which are nonionogenic at a pH of less than or equal to 3 or which are potentially anionic at a higher pH, of those derived from ethylenically unsaturated monomers, such as monomers having at least one carboxyl functional group, such as α,β-ethylenically unsaturated carboxylic acid or the corresponding anhydrides, such as acrylic acid, methacrylic acid, maleic acid, acrylic anhydride, methacrylic anhydride, maleic anhydride, fumaric acid, itaconic acid, N-methacroyloylalanine, N-acryloylglycine and their water-soluble salts, monomers which are precursors of carboxylate functional groups, such as tert-butyl acrylate, which generate, after polymerization, carboxyl functional groups by hydrolysis.

Mention may be made, among the units which are nonionogenic at a pH of greater than or equal to 9, of those derived from ethylenically unsaturated monomers, such as ω-(N,N-dialkylamino)alkyl amides of α,β-mono-ethylenically unsaturated carboxylic acids, such as N,N-dimethylaminomethylacrylamide or -methacrylamide, 2-(N,N-dimethylamino)ethylacrylamide or -methacrylamide, 3-(N,N-dimethylamino)propylacrylamide or -methacrylamide, or 4-(N,N-dimethylamino)butylacrylamide or -methacrylamide, α,β-monoethylenically unsaturated amino esters, such as 2-(dimethylamino)ethyl methacrylate (DMAM), 3-(dimethylamino)propyl methacrylate, 2-(tert-butylamino)ethyl methacrylate, 2-(dipentylamino)ethyl methacrylate or 2-(diethylamino)ethyl methacrylate, monomers which are precursors of amine functional groups, such as N-vinylformamide, N-vinylacetamide, and the like, which generate primary amine functional groups by simple acidic or basic hydrolysis.

Mention may be made, among the anionic units (the first pKa of which is less than 3), of monomers having at least one sulfate or sulfonate functional group, such as 2-sulfooxyethyl methacrylate, vinylbenzenesulfonic acid, allylsulfonic acid, 2-acrylamido-2-methylpropanesulfonic acid, sulfoethyl acrylate or methacrylate, sulfopropyl acrylate or methacrylate, and their water-soluble salts, monomers having at least one phosphonate or phosphate functional group, such as vinylphosphonic acid, and the like, ethylenically unsaturated phosphate esters, such as phosphates derived from hydroxyethyl methacrylate (Empicryl 6835 from Rhodia) and those derived from polyoxyalkylene methacrylates, and their water-soluble salts.

Preferably, the polybetaine (B) does not comprise monomer units other than betaines carrying as many permanent anionic charges as permanent cationic charges at a pH ranging from 1 to 14. If other units are present, they are rather potentially anionic units in an amount of less than 50 mol %, preferably of less than 30 mol %.

Said polybetaine (B) can be obtained in particular by radical polymerization or copolymerization in aqueous solution of ethylenically unsaturated betaine monomers, in particular of ethylenically unsaturated monomers carrying at least one betaine functional group of formula (I) to (X) above, and optionally of other ethylenically unsaturated monomers.

Said monomers can exhibit, by way of examples:

one or more mono- or polyethylenically unsaturated hydrocarbon radicals (in particular vinyl, allyl or styryl radicals, and the like)

one or more mono- or polyethylenically unsaturated ester radicals (in particular acrylate, methacrylate or maleate radicals, and the like)

one or more mono- or polyethylenically unsaturated amide radicals (in particular acrylamido or methacrylamido radicals, and the like).

Mention may in particular be made, by way of examples, of polybetaines derived from the following betaine monomers:

alkyl or hydroxyalkyl sulfonates or phosphonates of dialkylammonium alkyl acrylates or methacrylates, acrylamido or methacrylamido, such as:

sulfopropyldimethylammonioethyl methacrylate, sold by Raschig under the name SPE:

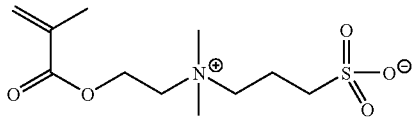

(SPE)

sulfoethyldimethylammonioethyl methacrylate and sulfobutyldimethylammonioethyl methacrylate:

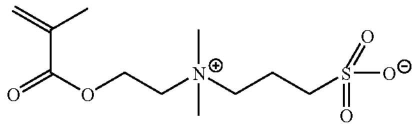

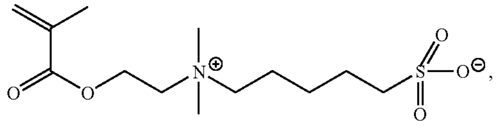

the synthesis of which is described in the paper "Sulfobetaine zwitterionomers based on n-butyl acrylate and 2-ethoxyethyl acrylate: monomer synthesis and copolymerization behavior", Journal of Polymer Science, 40, 511-523 (2002), sulfohydroxypropyldimethylammonioethyl methacrylate:

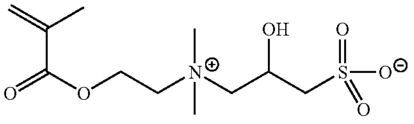

sulfopropyldimethylammoniopropylacrylamide:

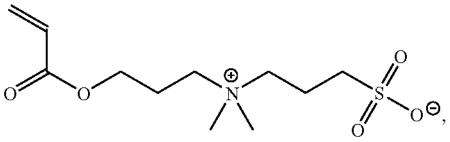

the synthesis of which is described in the paper "Synthesis and solubility of the poly(sulfobetaine)s and the corresponding cationic polymers: 1. Synthesis and characterization of sulfobetaines and the corresponding cationic monomers by nuclear magnetic resonance spectra", Wen-Fu Lee and Chan-Chang Tsai, Polymer, 35 (10), 2210-2217 (1994), sulfopropyldimethylammoniopropylmethacrylamide, sold by Raschig under the name SPP:

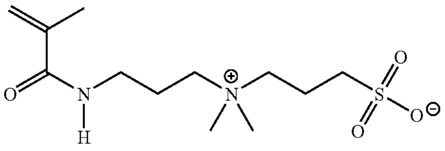

(SPP)

sulfohydroxypropyldimethylammoniopropylmethacrylamide:

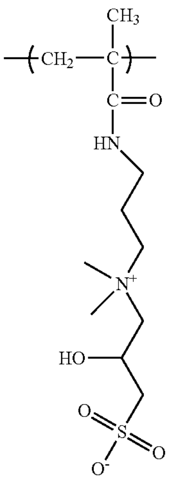

(-SHPP-)

sulfopropyldiethylammonioethyl methacrylate:

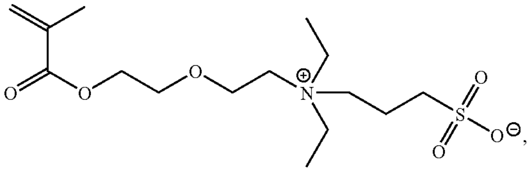

the synthesis of which is described in the paper "Poly(sulphopropylbetaines): 1. Synthesis and characterization", V. M. Monroy Soto and J. C. Galin, Polymer, 1984, Vol. 25, 121-128, heterocyclic betaine monomers, such as:

sulfobetaines derived from piperazine:

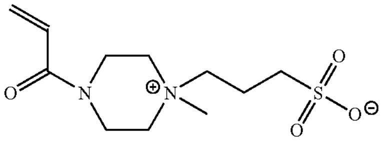

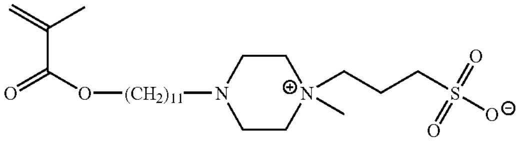

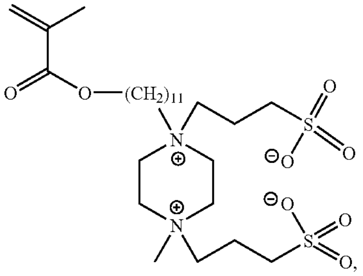

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), sulfobetaines derived from 2-vinylpyridine and 4-vinylpyridine, such as 2-vinyl-1-(3-sulfopropyl)pyridinium betaine (2SPV), sold by Raschig under the name SPV:

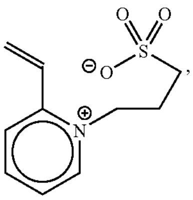

(2SPV)

and 4-vinyl-1-(3-sulfopropyl)pyridinium betaine (4SPV), the synthesis of which is disclosed in the paper "Evidence of ionic aggregates in some ampholytic polymers by transmission electron microscopy", V. M. Castaño and A. E. González, J. Cardoso, O. Manero and V. M. Monroy, J. Mater. Res., 5 (3), 654-657 (1990):

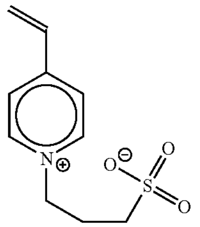

(4SPV)

1-vinyl-3-(3-sulfopropyl)imidazolium betaine:

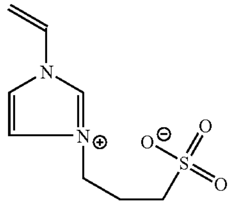

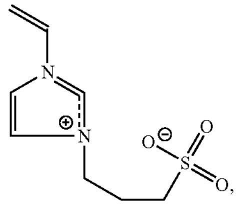

the synthesis of which is described in the paper "Aqueous solution properties of a poly(vinyl imidazolium sulphobetaine)", J. C. Salamone, W. Volkson, A. P. Oison, S. C. Israel, Polymer, 19, 1157-1162 (1978), alkyl or hydroxyalkyl sulfonates or phosphonates of dialkylammonium alkyl allylics, such as sulfopropylmethyldiallylammonium betaine:

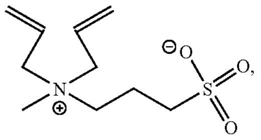

the synthesis of which is described in the paper "New poly (carbobetaine)s made from zwitterionic diallylammonium monomers", Favresse, Philippe; Laschewsky, Andre, Macromolecular Chemistry and Physics, 200(4), 887-895 (1999), alkyl or hydroxyalkyl sulfonates or phosphonates of dialkylammonium alkyl styrenes, such as:

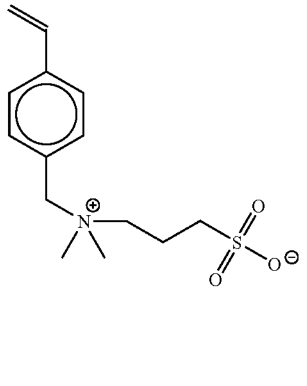

-continued

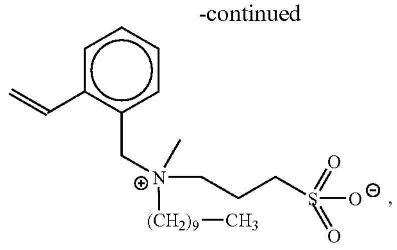

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), betaines resulting from ethylenically unsaturated anhydrides and dienes, such as:

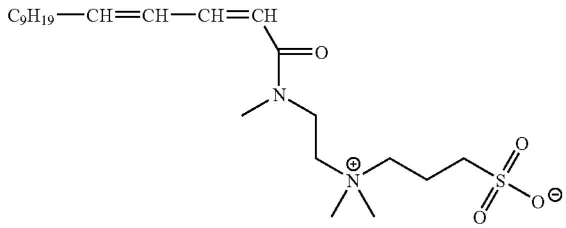

and

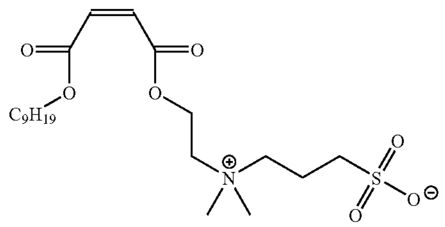

the synthesis of which is described in the paper "Hydrophobically Modified Zwitterionic Polymers: Synthesis, Bulk Properties, and Miscibility with Inorganic Salts", P. Koberle and A. Laschewsky, Macromolecules, 27, 2165-2173 (1994), phosphobetaines, such as:

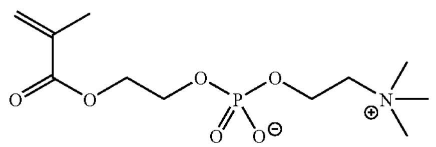

(MPC)

or alternatively:

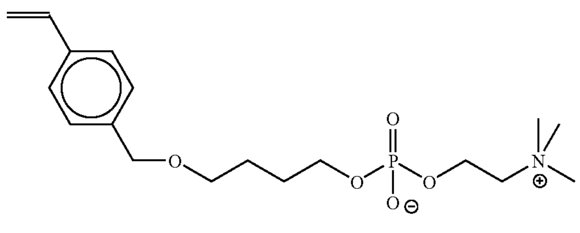

(VPC)

The synthesis of MPC and of VPC is disclosed in EP 810 239 B1 (Biocompatibles, Alister et al.).

betaines resulting from cyclic acetals, such as ((dicyanoethanolate)ethoxy)dimethylammoniumpropylmethacrylamide:

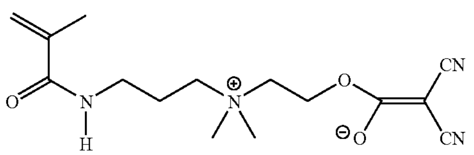

the synthesis of which is described by M-L. Pujol-Fortin et al. in the paper "Poly(ammonium alkoxydicyanatoethenolates) as new hydrophobic and highly dipolar poly(zwitterions). 1. Synthesis", Macromolecules, 24, 4523-4530 (1991).

Said polybetaines (B) according to the invention can also be obtained in a known way by chemical modification of a polymer referred to as a precursor polymer. Thus, a polysulfobetaine can be obtained by chemical modification, using a sultone (propane sultone, butane sultone), a haloalkylsulfonate or any other sulfonated electrophilic compound, of a polymer comprising pendent amine functional groups.

A few synthetic examples are given below:

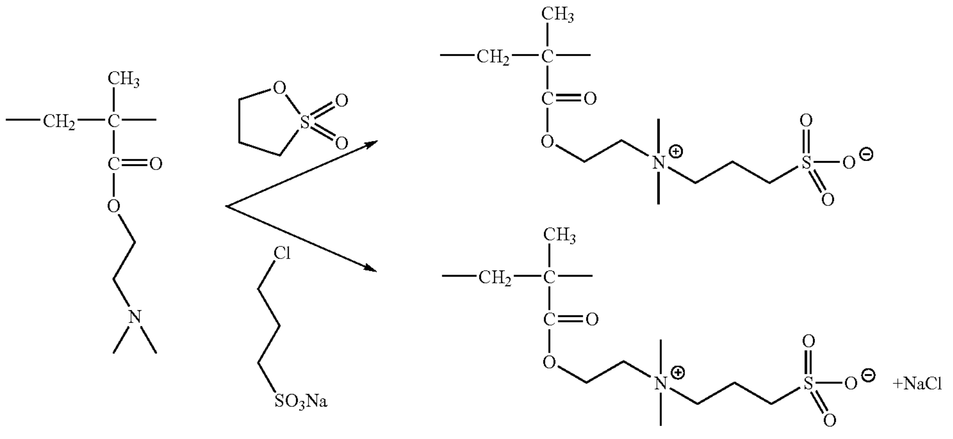

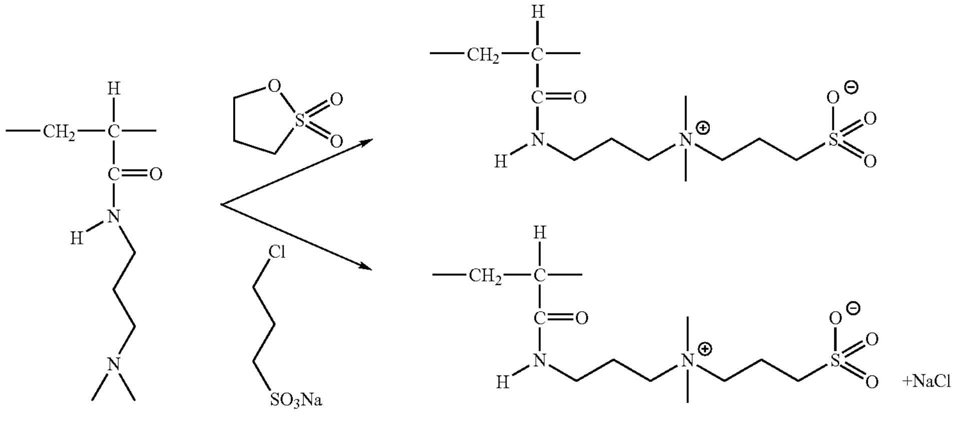

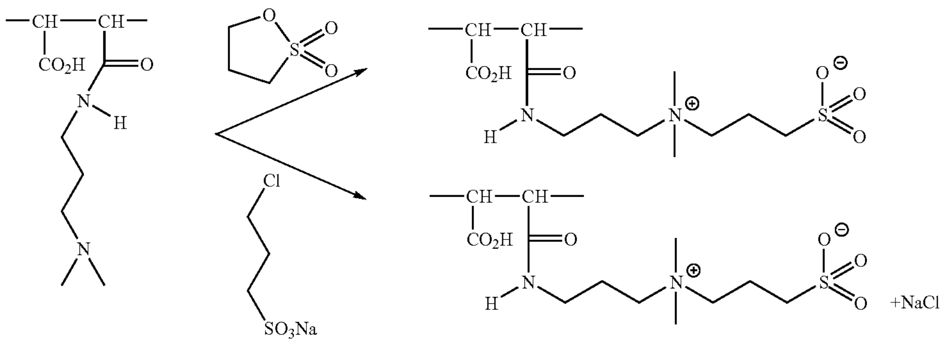

The main routes of access to polysulfobetaines by chemical modification of a precursor polymer by sultones and haloalkylsulfonates are described in particular in the following documents:

"Synthesis and aqueous solution behaviour of copolymers containing sulfobetaine moieties in side chains", I. V. Berlinova, I. V. Dimitrov, R. G. Kalinova, N. G. Vladimirov, Polymer, 41, 831-837 (2000)

"Poly(sulfobetaine)s and corresponding cationic polymers: 3. Synthesis and dilute aqueous solution properties of poly(sulfobetaine)s derived from styrene-maleic anhydride", Wen-Fu Lee and Chun-Hsiung Lee, Polymer, 38 (4), 971-979 (1997)

"Poly(sulfobetaine)s and corresponding cationic polymers. VIII. Synthesis and aqueous solution properties of a cationic poly(methyl iodide quaternized styrene-N,N-dimethylaminopropyl maleamidic acid) copolymer", Lee, Wen-Fu and Chen, Yan-Ming, Journal of Applied Polymer Science, 80, 1619-1626 (2001)

"Synthesis of polybetaines with narrow molecular mass distribution and controlled architecture", Andrew B. Lowe, Norman C. Billingham and Steven P. Armes, Chem. Commun., 1555-1556 (1996)

"Synthesis and Properties of Low-Polydispersity Poly(sulfopropylbetaine)s and Their Block Copolymers", Andrew B. Lowe, Norman C. Billingham and Steven P. Armes, Macromolecules, 32, 2141-2146 (1999)

Japanese patent application published on 21 Dec. 1999 under the number 11-349826.

The preparation of polyphosphonato- and phosphinatobetaines by chemical modification is reported in "New polymeric phosphonato-, phosphinato- and carboxybetaines", T. Hamaide, Macromolecular Chemistry, 187, 1097-1107 (1986).

Preferably, the polybetaine B is chosen from alkylsulfonates or hydroxyalkylsulfonates of dialkylammonium alkyl methacrylates or methacrylamides and sulfobetaines derived from a vinylpyridine. More preferably still, they are alkylsulfonates or hydroxyalkylsulfonates of dialkylammonium methacrylamides.

Thus, preferably, the polybetaine B is chosen from:

homopolymers formed of betaine units chosen from those of following formulae (-SPE-), (-SPP-), (-SHPE-) and (-SHPP-)

(-SPE-)

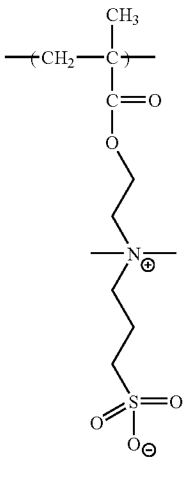

-continued (-SPP-)

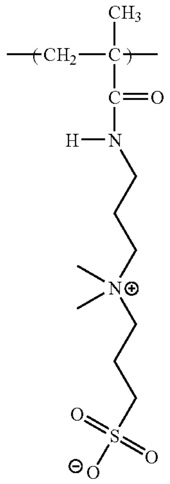

(-SHPE-)

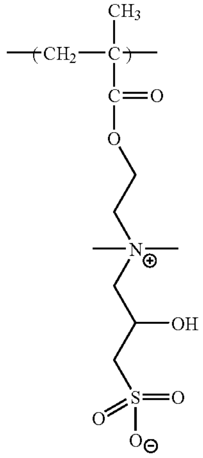

(-SHPP-)

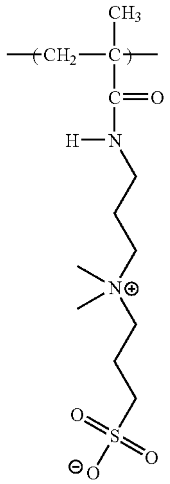

homopolymers of sulfobetaine which is derived from 2-vinylpyridine of formula

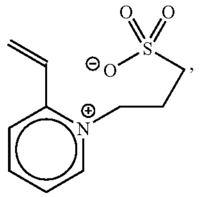

(2SPV)

copolymers formed of betaine units, at least two of which are different and are chosen from those of formulae (-SPE-), (-SPP-), (-SHPE-) and (-SHPP-) above copolymers formed of identical or different betaine units chosen from those of formulae (-SPE-), (-SPP-), (-SHPE-) and (-SHPP-) above and of methacrylic acid units, the amount of methacrylic acid units representing less than 50 mol %, preferably less than 30 mol %, of said copolymers.

Very preferably, the homopolymers or copolymers comprising betaine units chosen from those of formulae (-SPE-), (-SPP-), (-SHPE-) and (-SHPP-) exhibit an absolute weight-average molar mass ($M_w$) ranging from 10 000 to 150 000 g/mol.

The cleaning or rinsing composition according to the invention additionally comprises at least one surface-active agent. The latter can be nonionic, anionic, amphoteric, zwitterionic or cationic.

Mention may be made, among anionic surface-active agents, by way of examples, of:

alkyl ester sulfonates of formula R—CH($SO_3$M)—COOR', where R represents a $C_8$-$C_{20}$, preferably $C_{10}$-$C_{16}$, alkyl radical, R' represents a $C_1$-$C_6$, preferably $C_1$-$C_3$, alkyl radical and M represents an alkali metal (sodium, potassium or lithium) cation, a substituted or unsubstituted ammonium (methyl-, dimethyl-, trimethyl- or tetramethylammonium, dimethylpiperidinium, and the like) cation or a cation derived from an alkanolamine (monoethanolamine, diethanolamine, triethanolamine, and the like). Mention may very particularly be made of methyl ester sulfonates in which the R radical is $C_{14}$-$C_{16}$ radical;

alkyl sulfates of formula $ROSO_3M$, where R represents a $C_5$-$C_{24}$, preferably $C_{10}$-$C_{18}$, alkyl or hydroxyalkyl radical (such as salts of fatty acids derived from copra and tallow), M representing a hydrogen atom or a cation with the same definition as above, and their ethoxylenated (EO) and/or propoxylenated (PO) derivatives, having on average from 0.5 to 30, preferably from 0.5 to 10, EO and/or PO units;

alkylamide sulfates of formula $RCONHR'OSO_3M$, where R represents a $C_2$-$C_{22}$, preferably $C_6$-$C_{20}$, alkyl radical and R' represents a $C_2$-$C_3$ alkyl radical, M representing a hydrogen atom or a cation with the same definition as above, and their ethoxylenated (EO) and/or propoxylenated (PO) derivatives, having on average from 0.5 to 60 EO and/or PO units;

salts of saturated or unsaturated $C_8$-$C_{24}$, preferably $C_{14}$-$C_{20}$, fatty acids, $C_9$-$C_{20}$ alkylbenzenesulfonates, primary or secondary $C_8$-$C_{22}$ alkylsulfonates, alkylglycerolsulfonates, the sulfonated polycarboxylic acids disclosed in GB-A-1 082 179, paraffin sulfonates, N-acyl-N-alkyltaurates, isethionates, alkylsuccinamates, alkylsulfosuccinates, monoesters or diesters of sulfosuccinates, N-acylsarcosinates, alkylglycoside sulfates, polyethoxycarboxylates, monoglyceride sulfates and condensates of fatty acid chlorides with hydroxyalkylsulfonates; the cation can be an alkali metal (sodium, potassium or lithium), a substituted or unsubstituted ammonium (methyl-, dimethyl-, trimethyl- or tetramethylammonium, dimethylpiperidinium, and the like) residue, or a residue derived from an alkanolamine (monoethanolamine, diethanolamine, triethanolamine, and the like);

alkyl phosphates, or alkyl or alkylaryl phosphate esters, such as Rhodafac RA600, Rhodafac PA15 or Rhodafac PA23, sold by Rhodia; the cation can be an alkali metal (sodium, potassium or lithium), a substituted or unsubstituted ammonium (methyl-, dimethyl-, trimethyl- or tetramethylammonium, dimethylpiperidinium, and the like) residue, or a residue derived from an alkanolamine (monoethanolamine, diethanolamine, triethanolamine, and the like).

A description of nonionic surface-active agents is given in U.S. Pat. Nos. 4,287,080 and 4,470,923. Mention may in particular be made of condensates of alkylene oxide, in particular of ethylene oxide and optionally of propylene oxide, with alcohols, polyols, alkylphenols, fatty acid esters, fatty acid amides and fatty amines; amine oxides; sugar derivatives, such as alkylpolyglycosides or esters of fatty acids and of sugars, in particular sucrose monopalmitate; long-chain (of 8 to 28 carbon atoms) tertiary phosphine oxides; dialkyl sulfoxides; block copolymers of polyoxyethylene and of polyoxypropylene; polyalkoxylated esters of sorbitan; fatty esters of sorbitan; poly(ethylene oxide)s and fatty acid amides modified so as to confer thereon a hydrophobic nature (for example, fatty acid mono- and diethanolamides comprising from 10 to 18 carbon atoms).

Mention may very particularly be made of:

polyoxyalkylenated $C_8$-$C_{18}$ aliphatic carboxylic acids comprising from 2 to 50 oxyalkylene (oxyethylene and/or oxypropylene) units, in particular of those with 12 (mean) carbon atoms or with 18 (mean) carbon atoms, polyoxyalkylenated $C_6$-$C_{24}$ aliphatic alcohols comprising from 2 to 50 oxyalkylene (oxyethylene and/or oxypropylene) units, in particular of those with 12 (mean) carbon atoms or with 18 (mean) carbon atoms; mention may be made of Antarox B12DF, Antarox FM33, Antarox FM63 and Antarox V74 from Rhodia, Plurafac LF 400 and Plurafac LF 220 from BASF, Rhodasurf ID 060, Rhodasurf ID 070 and Rhodasurf LA 42 from Rhodia and Synperonic AS, A7 and A9 from ICI, amine oxides, such as dodecyldi(2-hydroxyethyl)amine oxide, phosphine oxides, such as tetradecyldimethylphosphine oxide.

Mention may be made, among amphoteric surface-active agents, of:

sodium iminodipropionates or alkyliminopropionates, such as Mirataine $H_2C$ HA and Mirataine JC HA from Rhodia, alkyl amphoacetates or alkyl amphodiacetates, the alkyl group of which comprises from 6 to 20 carbon atoms, such as Miranol C2M Conc NP, sold by Rhodia, amphoteric alkylpolyamine derivatives, such as Amphionic XL®, sold by Rhodia, and Ampholac 7T/X® and Ampholac 7C/X®, sold by Berol Nobel.

Mention may be made, among zwitterionic surface-active agents, of those disclosed in U.S. Pat. No. 5,108,660. The preferred zwitterionic surfactants are alkyl dimethyl betaines, alkyl amidopropyldimethyl betaines, alkyl dimethyl sulfobetaines or alkyl amidopropyldimethyl sulfobetaines, such as Mirataine JCHA, Mirataine H2CHA or Mirataine CBS, sold by Rhodia, or those of the same type sold by Sherex Company under the name of "Varion CADG Betaine" and "Varion CAS Sulfobetaine", or the condensation products of fatty acids and of protein hydrolysates.

Other zwitterionic surfactants are also disclosed in U.S. Pat. No. 4,287,080 and in U.S. Pat. No. 4,557,853.

Mention may in particular be made, among cationic surface-active agents, of the quaternary ammonium salts of formula $R^1R^2R^3R^4N^+X^-$ where

- $R^1$, $R^2$ and $R^3$, which are identical or different, represent H or an alkyl group comprising less than 4 carbon atoms, preferably 1 or 2 carbon atom(s), which is optionally substituted by one or more hydroxyl functional group(s), or can form, together with the nitrogen atom $N^+$, at least one aromatic or heterocyclic ring,
- $R^4$ represents a $C_8$-$C_{22}$, preferably $C_{12}$-$C_{22}$, alkyl or alkenyl group or an aryl or benzyl group, and
- $X^-$ is a solubilizing anion, such as halide (for example, chloride, bromide or iodide), sulfate or alkyl sulfate (methyl sulfate), carboxylate (acetate, propionate or benzoate), alkylsulfonate or arylsulfonate.

Mention may in particular be made of dodecyltrimethylammonium bromide, tetradecyltrimethylammonium bromide, cetyltrimethylammonium bromide, stearylpyridinium chloride, Rhodaquat® TFR and Rhodamine® C15, which are sold by Rhodia, cetyltrimethylammonium chloride (Dehyquart ACA and/or AOR from Cognis) or cocobis(2-hydroxyethyl) ethylammonium chloride (Ethoquad C12 from Akzo Nobel).

Mention may also be made of other cationic surface-active agents, such as:

quaternary ammonium salts of formula $R^{1'}R^{2'}R^{3'}R^{4'}N^+X^-$ where

- $R^1$ and $R^2$, which are identical or different, represent H or an alkyl group comprising less than 4 carbon atoms, preferably 1 or 2 carbon atom(s), which is optionally substituted by one or more hydroxyl functional group(s), or can form, together with the nitrogen atom $N^+$, a heterocyclic ring,
- $R^{3'}$ and $R^{4'}$ represent a $C_8$-$C_{22}$, preferably $C_{10}$-$C_{22}$, alkyl or alkenyl group or an aryl or benzyl group, and
- $X^-$ is an anion, such as halide (for example, chloride, bromide or iodide), sulfate or alkyl sulfate (methyl sulfate), carboxylate (acetate, propionate or benzoate), alkylsulfonate or arylsulfonate.

Mention may in particular be made of: dialkydimethylammonium chlorides, such as ditallowdimethylammonium chloride or methyl sulfate, and the like, or alkylbenzyldimethylammonium chlorides.

- $(C_{10}$-$C_{25})$alkylimidazolium salts, such as $(C_{10}$-$C_{25})$alkylimidazolinium methyl sulfates,
- salts of substituted polyamines, such as N-tallow-N,N',N'-triethanol-1,3-propylenediamine dichloride or di(methyl sulfate) or N-tallow-N,N,N',N',N'-pentamethyl-1,3-propylenediamine dichloride.

Additional examples of appropriate surfactants are compounds generally used as surface-active agents denoted in the well-known handbook "Surface Active Agents", volume I, by Schwartz and Perry, and "Surface Active Agents and Detergents", volume II, by Schwartz, Perry and Berch.

The surface-active agents represent from 0.005 to 60%, in particular from 0.5 to 40%, of the weight of the composition of the invention, this being according to the nature of the surface-active agent(s) and the destination of the cleaning composition.

Advantageously, the polybetaine (B)/surface-active agent(s) ratio by weight is between 1/1 and 1/1000, advantageously 1/2 and 1/200.

The cleaning or rinsing composition according to the invention can additionally comprise at least one other additive chosen in particular from conventional additives present in compositions for cleaning or rinsing hard surfaces.

Mention may in particular be made of:

- chelating agents, in particular of the water-soluble aminophosphonates and organic phosphonates type, such as
- 1-hydroxyethane-1,1-diphosphonates,
- aminotri(methylenediphosphonate),
- vinyldiphosphonates,
- salts of oligomers or polymers of vinylphosphonic or vinyldiphosphonic acid,
- salts of random cooligomers or copolymers of vinylphosphonic or vinyldiphosphonic acid and of acrylic acid and/or of maleic anhydride and/or of vinylsulfonic acid and/or of acrylamidomethylpropane-sulfonic acid,
- salts of phosphonated polycarboxylic acids,
- polyacrylates comprising phosphonate ending(s),
- salts of cotelomers of vinylphosphonic or vinyldiphosphonic acid and of acrylic acid, such as those of the Briquest® range or Mirapol A300 or 400 from Rhodia (in a proportion of 0 to 10%, preferably of 0 to 5%, of the total weight of cleaning composition);

- sequestering or scale-inhibiting agents, such as
  - polycarboxylic acids or their water-soluble salts and water-soluble salts of carboxylic polymers or copolymers, such as
    - polycarboxylates or hydroxypolycarboxylate ethers,
    - polyacetic acids or their salts (nitriloacetic acid, N,N-dicarboxymethyl-2-aminopentanedioic acid, ethylenediaminetetraacetic acid, diethylenetriaminepentaacetic acid, ethylenediaminetetraacetates, nitriloacetates or N-(2-hydroxyethyl)nitrilodiacetates),
    - salts of $(C_5$-$C_{20}$ alkyl)succinic acids,
    - polycarboxylic acetal esters,
    - salts of polyaspartic or polyglutamic acids,
    - citric acid, adipic acid, gluconic acid or tartaric acid, or their salts,
  - copolymers of acrylic acid and of maleic anhydride or acrylic acid homopolymers, such as Rhodoline DP 226 35 from Rhodia and Sokalan CP5 from BASF (in a proportion of 0 to 10% of the total weight of said cleaning composition),
  - sulfonated polyvinylstyrenes or their copolymers with acrylic acid, methacrylic acid, and the like, (in a proportion of 0 to 10% of the total weight of cleaning composition);

- inorganic builders (detergency adjuvants which improve the surface properties of surfactants) of the type:
  - alkali metal, ammonium or alkanolamine polyphosphates, such as Rhodiaphos HD7, sold by Rhodia (in a proportion of 0 to 70% of the total weight of cleaning composition),
  - alkali metal pyrophosphates,
  - alkali metal silicates with an $SiO_2/M_2O$ ratio which can range from 1 to 4, preferably from 1.5 to 3.5, very particularly from 1.7 to 2.8; they can be amorphous silicates or lamellar silicates, such as the α, β, γ and δ phases of $Na_2Si_2O_5$, sold under the references NaSKS-5, NaSKS-7, NaSKS-11 and NaSKS-6 by Clariant, alkali metal or alkaline earth metal borates, carbonates, bicarbonates or sesquicarbonates (in an amount which can range up to approximately 50% of the total weight of said cleaning composition), cogranules of alkali metal silicate hydrates, with an $SiO_2/M_2O$ ratio which can range from 1.5 to 3.5, and of alkali metal (sodium or potassium) carbonates; mention may in particular be made of the cogranules in which the content by weight of water associated with the silicate with respect to the dry silicate is at least 33/100, it being possible for the ratio by weight of the silicate to the carbonate to range from 5/95 to 45/55, preferably from 15/85 to 35/65, such as disclosed in EP-A-488 868 and EP-A-561 656, for example Nabion 15, sold by Rhodia, (it being possible for the total amount of builders to represent up to 90% of the total weight of said cleaning or rinsing composition);

bleaching agents of the perborates or percarbonates type, which may or may not be combined with acetylated bleaching activators, such as N,N,N',N'-tetraacetylethylenediamine (TAED), or chlorinated products of the chloroisocyanurates type, or chlorinated products of the alkali metal hypochlorites type, or aqueous hydrogen peroxide solution (in a proportion of 0 to 30% of the total weight of said cleaning composition);

fillers of the sodium sulfate, sodium chloride, sodium carbonate, calcium carbonate, kaolin or silica type, in a proportion of 0 to 50% of the total weight of said composition;

bleaching catalysts comprising a transition metal, in particular iron, manganese and cobalt complexes, such as those of the type $[Mn^{IV}_2(\mu\text{-}O)_3(Me_3TACN)_2](PF_6)_2$, $[Fe^{II}(MeN_4py)(MeCN)](ClO_4)_2$, $[(CO^{III})(NH_3)_5(OAc)](OAc)_2$, disclosed in U.S. Pat. Nos. 4,728,455, 5,114,606, 5,280,117, EP-A-909 809, U.S. Pat. No. 5,559,261, WO 96/23859, 96/23860 and 96/23861 (in a proportion of 0 to 5% of the total weight of said cleaning composition);

agents which influence the pH of the composition, which are soluble in the cleaning or rinsing medium, in particular basifying additives (alkali metal phosphates, carbonates, perborates or alkali metal hydroxides) or optionally cleaning acidifying additives, such as inorganic acids (phosphoric, polyphosphoric, sulfamic, hydrochloric, hydrofluoric, sulfuric, nitric or chromic acid), carboxylic or polycarboxylic acids (acetic, hydroxyacetic, adipic, citric, formic, fumaric, gluconic, glutaric, glycolic, malic, maleic, lactic, malonic, oxalic, succinic and tartaric acid), or salts of acids, such as sodium bisulfate or alkali metal bicarbonates and sesquicarbonates;

polymers used to control the viscosity of the mixture and/or the stability of the foams formed during use, such as cellulose derivatives or guar derivatives (carboxymethylcellulose, hydroxyethylcellulose, hydroxypropylguar, carboxymethylguar, carboxymethyl-hydroxypropylguar, and the like), xanthan gum, succinoglycan (Rheozan® sold by Rhodia), locust bean gum or carrageenans (in a proportion of 0 to 2% of the total weight of said cleaning composition);

hydrotropic agents, such as short-chain $C_2$-$C_8$ alcohols, in particular ethanol, diols and glycols, such as diethylene glycol or dipropylene glycol, sodium xylenesulfonate or sodium naphthalenesulfonate (in a proportion of 0 to 10 g per 100 g of said cleaning composition);

hydrating or moisturizing agents for the skin, such as glycerol or urea, or agents for protecting the skin, such as proteins or protein hydrolysates, vegetable oils, such as soybean oil, or cationic polymers, such as cationic guar derivatives (Jaguar C13S®, Jaguar C162® or Hicare 1000®, sold by Rhodia) (in a proportion of 0 to 40% of the total weight of said cleaning composition);

biocides or disinfectants, such as cationic biocides, for example mono(quaternary ammonium) salts, such as cocoalkylbenzyldimethylammonium, ($C_{12}$-$C_{14}$ alkyl)benzyldimethylammonium, cocoalkyldichlorobenzyldimethylammonium, tetradecylbenzyldimethylammonium, didecyldimethylammonium or dioctyldimethylammonium chlorides, myristyltrimethylammonium or cetyltrimethylammonium bromides, monoquaternary heterocyclic amine salts, such as laurylpyridinium, cetylpyridinium or ($C_{12}$-$C_{14}$ alkyl)benzylimidazolium chlorides, (fatty alkyl)triphenylphosphonium salts, such as myristyltriphenylphosphonium bromide, polymeric biocides, such as those derived from the reaction of epichlorohydrin and of dimethylamine or of diethylamine, of epichlorohydrin and of imidazole, of 1,3-dichloro-2-propanol and of dimethylamine, of 1,3-dichloro-2-propanol and of 1,3-bis(dimethylamino)-2-propanol, of ethylene dichloride and of 1,3-bis(dimethylamino)-2-propanol, of bis(2-chloroethyl) ether and of N,N'-bis(dimethylaminopropyl)urea or -thiourea, biguanidine polymer hydrochlorides, such as Vantocil IB, amphoteric biocides, such as N—[N'—($C_8$-$C_{18}$ alkyl)-3-aminopropyl]glycine, N—{N'—[N"—($C_8$-$C_{18}$ alkyl)-2-aminoethyl]-2-aminoethyl}glycine or N,N-bis[N'-($C_8$-$C_{18}$ alkyl)-2-aminoethyl]glycine derivatives, such as (dodecyl)(aminopropyl)glycine or (dodecyl)(diethylenediamine)glycine, amines, such as N-(3-aminopropyl)-N-dodecyl-1,3-propanediamine, halogenated biocides, such as iodophores and hypochlorite salts, such as sodium dichloroisocy-n-urate, phenolic biocides, such as phenol, resorcinol, cresols or salicylic acid, hydrophobic biocides, such as, para-chloro-meta-xylenol or dichloro-meta-xylenol, 4-chloro-m-cresol, resorcinol monoacetate, mono- or polyalkyl or -aryl phenols, cresols or resorcinols, such as o-phenylphenol, p-tert-butylphenol, or 6-(n-amyl)-n-cresol, alkyl and/or aryl chloro- or bromophenols, such as o-benzyl-p-chlorophenol, halogenated diphenyl ethers, such as 2',4,4'-trichloro-2-hydroxydiphenyl ether (triclosan) or 2,2'-dihydroxy-5,5'-dibromodiphenyl ether, chlorphenesin (p-chlorophenyl glyceryl ether), in a proportion of 0 to 50% of the total weight of said cleaning composition;

solvents having a good cleaning or degreasing activity, such as alkylbenzenes of octylbenzene type, olefins having a boiling point of at least 100° C., such as α-olefins, preferably 1-decene or 1-dodecene, glycol ethers of general formula $R1O(R2O)_mH$, where R1 is an alkyl group exhibiting from 3 to 8 carbons and each R2 is either an ethylene or propylene and m is a number which varies from 1 to 3; mention may be made of monopropylene glycol monopropyl ether, dipropylene glycol monobutyl ether, monopropylene glycol monobutyl ether, diethylene glycol monohexyl ether, monoethylene glycol monohexyl ether, monoethylene glycol monobutyl ether and their mixtures, diols exhibiting from 6 to 16 carbon atoms in their molecular structure; diols are particularly advantageous as, in addition to their degreasing properties, they can help in removing calcium salts (soaps); diols comprising from 8 to 12 carbon atoms are preferred, very particularly 2,2,4-trimethyl-1,3-pentanediol, other solvents, such as pine oil, orange terpenes, benzyl alcohol, n-hexanol, phthalic esters of alcohols having 1 to 4 carbon atoms, butoxy propanol, Butyl Carbitol and 1-(2-(n-butoxy)-1-methylethoxy)propan-2-ol, also known as butoxypropoxy propanol or dipropylene glycol monobutyl ether, diglycol hexyl (Hexyl Carbitol), butyl triglycol, diols, such as 2,2,4-trimethyl-1,3-pentanediol, and their mixtures, (in a proportion of 0 to 30% of the total weight of said cleaning composition);

industrial cleaners, such as solutions of alkali metal salts of the phosphate, carbonate, silicate, and the like, type of sodium or potassium (in a proportion of 0 to 50% of the total weight of said cleaning composition);

water-soluble organic solvents with little cleaning effect, such as methanol, ethanol, isopropanol, ethylene glycol, propylene glycol and their mixtures (in a proportion of 0 to 40% of the total weight of said cleaning composition);

cosolvents, such as monoethanolamide and/or β-aminoalkanols, which are particularly advantageous in compositions with a pH of greater than 11, very particularly of greater than 11.7, as they help in reducing the formation of films and marks on hard surfaces (they can be employed in a proportion of 0.05 to 5% of the weight of the cleaning composition); solvent systems comprising monoethanolamide and/or β-aminoalkanols are disclosed in U.S. Pat. No. 5,108,660;

antifoaming agents, such as soaps in particular. Soaps are alkali metal salts of fatty acids, in particular sodium, potassium, ammonium and alkanolammonium salts of higher fatty acids comprising approximately from 8 to 24 carbon atoms and preferably from approximately 10 to approximately 20 carbon atoms; mention may in particular be made of mono-, di- and triethanolamine, sodium and potassium salts of mixtures of fatty acids derived from coconut oil and from ground walnut oil. The amount of soap can be at least 0.005% by weight, preferably from 0.5 to 2% by weight, with respect to the total weight of the composition. Additional examples of foam modifiers are organic solvents, hydrophobic silica, silicone oil and hydrocarbons.

abrasives, such as silica or calcium carbonate;

various additives, such as enzymes, fragrances, colorants, agents which inhibit corrosion of metals, preservatives, optical brighteners, opacifying or pearlescent agents, and the like.

The pH of the composition forming the subject matter of the invention or the pH of use of said composition can range from 0.5 to 14, preferably from 1 to 14.

Compositions of alkaline type, with a pH of greater than or equal to 7.5, preferably of greater than 8.5, for domestic applications (very particularly with a pH from 8.5 to 12, in particular from 8.5 to 11.5) are of particular use for the removal of greasy soiling substances and are particularly well suited to the cleaning of kitchens.

They can comprise from 0.001 to 5%, preferably from 0.005 to 2%, of their weight of polybetaine (B).

The alkaline compositions generally comprise, in addition to the polybetaine (B), at least one additive chosen from a sequestering or scale-inhibiting agent (in an amount ranging from 0 to 40%, preferably from 1 to 40%, more preferably from 2 to 30% and very particularly from 5 to 20%, of the weight of the composition), a cationic biocide or disinfectant, in particular of quaternary ammonium type, such as (N-alkyl)benzyldimethylammonium chlorides, (N-alkyl)dimethyl(ethylbenzyl) ammonium chloride, N-didecyldimethylammonium halide and di(N-alkyl)dimethylammonium chloride (in an amount which can range from 0 to 60%, preferably from 0 to 40%, more preferably from 0 to 15% and very particularly from 0 to 5%, of the weight of the composition), at least one nonionic, amphoteric, zwitterionic or anionic surface-active agent or their mixture; when a cationic surface-active agent is present, said composition in addition preferably comprises an amphoteric and/or nonionic surface-active agent (the total amount of surface-active agents can range from 0 to 80%, preferably from 0 to 50%, very particularly from 0 to 35%, of the weight of the composition), if necessary, a pH modifier, in an amount which makes it possible to achieve, optionally after diluting or dissolving the composition, a pH of use ranging from 7.5 to 13; the pH modifier can in particular be a buffer system comprising monoethanolamine and/or a β-aminoalkanol and potentially but preferably "cobuffer" alkaline materials from the group consisting of aqueous ammonia, $C_2$-$C_4$ alkanolamines, silicates, borates, carbonates, bicarbonates, alkali metal hydroxides and their mixtures. The preferred cobuffers are alkali metal hydroxides.

from 0.5 to 98%, preferably from 25 to 95%, very particularly from 45 to 90%, by weight of water, a cleaning or degreasing organic solvent, in an amount which can represent from 0 to 60%, preferably from 1 to 45%, very particularly from 2 to 15%, of the weight of said composition, a cosolvent, such as monoethanolamine and/or β-aminoalkanols, in an amount which may represent from 0 to 10%, preferably from 0.05 to 10%, very particularly from 0.05 to 5%, by weight of said composition, a water-soluble organic solvent with little cleaning effect, in an amount which can represent from 0 to 25%, preferably from 1 to 20%, very particularly from 2 to 15%, of the weight of said composition, optionally a bleaching agent, a fragrance or other conventional additives.

Said alkaline compositions can be provided in the form of a ready-for-use formulation or else of a dry or concentrated formulation to be diluted in water in particular before use; they can be diluted from 1- to 10 000-fold, preferably from 1- to 1000-fold, before use.

Advantageously, a formulation for cleaning kitchens comprises:

from 0.001 to 1% by weight of polybetaine (B), from 1 to 10% by weight of water-soluble solvent, in particular isopropanol, from 1 to 5% by weight of cleaning or degreasing solvent, in particular butoxypropanol, from 0.1 to 2% by weight of monoethanolamine, from 0 to 5% by weight of at least one noncationic surface-active agent, preferably an amphoteric or nonionic surface-active agent, from 0 to 1% by weight of at least one cationic surface-active agent with a disinfecting property (in particular mixture of (n-alkyl)dimethyl(ethylbenzyl)ammonium chloride and (n-alkyl)dimethylbenzylammonium chloride), the total amount of surface-active agent(s) representing from 1 to 50% by weight, from 0 to 2% by weight of a dicarboxylic acid as scale-inhibiting agent, from 0 to 5% of a bleaching agent, and from 70 to 98% by weight of water.

The pH of such a formulation is preferably from 7.5 to 13, more preferably from 8 to 12.

Compositions of acidic type, with a pH of less than 5, are of particular use for the removal of soiling substances of inorganic type; they are particularly well suited to the cleaning of toilet bowls.

They can comprise from 0.001 to 5%, preferably from 0.01 to 2%, of their weight of polybetaine (B).

The acidic compositions generally comprise, in addition to the polybetaine (B), an inorganic or organic acidic agent (in an amount ranging from 0.1 to 40%, preferably from 0.5 to 20% and more preferably from 0.5 to 15%, of the weight of the composition), at least one nonionic, amphoteric, zwitterionic or anionic surface-active agent or their mixture (the total amount of surface-active agents can range from 0.5 to 20%, preferably from 0.5 to 10%, of the weight of the composition), optionally a cationic biocide or disinfectant, in particular of quaternary ammonium type such as (N-alkyl)benzyldimethylammonium chloride, (N-alkyl)dimethyl (ethylbenzyl)ammonium chloride, N-didecyldimethylammonium halide and di(N-alkyl)dimethylammonium chloride (in an amount which can range from 0.01 to 2%, preferably from 0.1 to 1%, of the weight of the composition), optionally a thickening agent (in an amount ranging from 0.1 to 3% of the weight of the composition), optionally a bleaching agent (in an amount ranging from 1 to 10% of the weight of the composition), from 0.5 to 99%, preferably from 50 to 98%, by weight of water, a solvent, such as glycol or an alcohol (in an amount which can range from 0 to 10%, preferably from 1 to 5%, of the weight of the composition), optionally a fragrance, a preservative, an abrasive or other conventional additives.

Said acidic compositions are preferably provided in the form of a ready-for-use formulation.

Advantageously, a formulation for cleaning toilet bowls comprises:

from 0.05 to 5%, preferably from 0.01 to 2%, by weight of polybetaine (B), an amount of acidic cleaning agent such that the final pH of the composition is from 0.5 to 4, preferably from 1 to 4; this amount is generally from 0.1 to approximately 40% and preferably between 0.5 and approximately 15% by weight, with respect to the weight of the composition; the acidic agent can be in particular an inorganic acid, such as phosphoric, sulfamic, hydrochloric, hydrofluoric, sulfuric, nitric or chromic acid and mixtures of these, an organic acid, in particular acetic, hydroxyacetic, adipic, citric, formic, fumaric, gluconic, glutaric, glycolic, malic, maleic, lactic, malonic, oxalic, succinic or tartaric acid and mixtures of these, or acid salts, such as sodium bisulfate, and mixtures of these; the preferred amount depends on the type of acidic cleaner used: for example, with sulfamic acid, it is between 0.2 and 10%, with hydrochloric acid between 1 and 15%, with citric acid between 2 and 15%, with formic acid between 5 and 15% and with phosphoric acid between 2 and 30%, by weight, from 0.5 to 10% by weight of at least one surface-active agent, preferably an anionic or nonionic surface-active agent, optionally from 0.1 to 2% by weight of at least one cationic surface-active agent with a disinfecting property (in particular mixture of (n-alkyl)dimethyl(ethylbenzyl)ammonium chloride and (n-alkyl)dimethylbenzylammonium chloride), optionally a thickening agent (in an amount ranging from 0.1 to 3% of the weight of the composition) of gum type, in particular a xanthan gum or a succinoglycan (Rheozan), optionally a bleaching agent (in an amount ranging from 1 to 10% of the weight of the composition), optionally a preservative, a colorant, a fragrance or an abrasive, and from 50 to 95% by weight of water.

A few other specific embodiments and forms of application of the composition of the invention are clarified below.

Thus, the composition according to the invention can be employed for making easier the cleaning treatment of glass surfaces, in particular of windows. This treatment can be carried out by the various known techniques. Mention may be made in particular of the techniques for cleaning windows by spraying with a jet of water using devices of the Kärcher® type.

The amount of polybetaine (B) introduced will generally be such that, during the use of the cleaning composition, after optional dilution, the concentration of polybetaine (B) is between 0.001 g/l and 2 g/l, preferably between 0.005 g/l and 0.5 g/l.

The composition for cleaning windows according to the invention comprises:

from 0.001 to 10%, preferably 0.005 to 3%, by weight of at least one polybetaine (B);

from 0.005 to 20%, preferably from 0.5 to 10%, by weight of at least one nonionic surface-active agent (for example an amine oxide or an alkyl polyglucoside) and/or anionic surface-active agent; and the remainder being formed of water and/or of various additives which are conventional in the field.

The cleaning formulations for windows comprising said polymer can also comprise:

from 0 to 10%, advantageously from 0.5 to 5%, of amphoteric surfactant, from 0 to 30%, advantageously from 0.5 to 15%, of solvent, such as alcohols, the remainder being composed of water and of conventional additives (in particular fragrances).

The pH of the composition is advantageously between 6 and 11.

The composition of the invention is also advantageous for making easier the cleaning of dishes in an automatic device. Said composition can be either a detergent (cleaning) formulation used in the washing cycle or a rinsing formulation.

The detergent compositions for washing dishes in automatic dishwashers according to the invention advantageously comprise from 0.01 to 5%, preferably 0.1 to 3%, by weight of polybetaine (B).

Said detergent compositions for dishwashers also comprise at least one surface-active agent, preferably a nonionic surface-active agent, in an amount which can range from 0.2 to 10%, preferably from 0.5 to 5%, of the weight of said detergent composition, the remainder being composed of various additives and of fillers, as already mentioned above.

Thus, they can additionally comprise

- up to 90% by weight of at least one detergency adjuvant (builder) of sodium tripolyphosphate or silicate type,
- up to 10%, preferably from 1 to 10%, very particularly from 2 to 8%, by weight of at least one auxiliary cleaning agent, preferably a copolymer of acrylic acid and of methylpropanesulfonic acid (AMPS),
- up to 30% by weight of at least one bleaching agent, preferably perborate or percarbonate, which may or may not be combined with a bleaching activator,
- up to 50% by weight of at least one filler, preferably sodium sulfate or sodium chloride.

The pH is advantageously between 8 and 13.

The compositions for making easier the rinsing of dishes in automatic dishwashers according to the invention can advantageously comprise from 0.02 to 10%, preferably from 0.1 to 5%, by weight of polybetaine (B), with respect to the total weight of the composition.

Said compositions can also comprise from 0.1 to 20%, preferably 0.2 to 15%, by weight, with respect to the total weight of said composition, of a surface-active agent, preferably a nonionic surface-active agent.

Mention may be made, among preferred nonionic surface-active agents of surface-active agents of the following types: polyoxyethylenated $C_6$-$C_{12}$ alkylphenols, polyoxyethylenated and/or polyoxypropylenated $C_8$-$C_{22}$ aliphatic alcohols, ethylene oxide/propylene oxide block copolymers, optionally polyoxyethylenated carboxamides, and the like.

Said compositions can additionally comprise from 0 to 10%, preferably from 0.5 to 5%, by weight, with respect to the total weight of the composition, of a calcium-sequestering organic acid, preferably citric acid.

They can also comprise an auxiliary agent of copolymer of acrylic acid and of maleic anhydride or acrylic acid homopolymers type, in a proportion of 0 to 15%, preferably 0.5 to 10%, by weight, with respect to the total weight of said composition.

The pH is advantageously between 4 and 7.

Another subject matter of the invention is a cleaning composition for making easier the washing of dishes by hand.

Preferred detergent formulations of this type comprise from 0.1 to 10 parts by weight of polybetaine (B) per 100 parts by weight of said composition and comprise from 3 to 50, preferably from 10 to 40, parts by weight of at least one surface-active agent, preferably an anionic surface-active agent, chosen in particular from sulfates of saturated $C_5$-$C_{24}$, preferably $C_8$-$C_{16}$, aliphatic alcohols, optionally condensed with approximately from 0.5 to 30, preferably 0.5 to 8, very particularly 0.5 to 5, mol of ethylene oxide, in the acid form or in the form of a salt, in particular an alkali metal (sodium) salt, alkaline earth metal (calcium, magnesium) salt, and the like.

Preferably, they are lathering liquid aqueous detergent formulations for making easier the washing of dishes by hand.

Said formulations can additionally comprise other additives, in particular other surface-active agents, such as:

- nonionic surface-active agents, such as amine oxides, alkylglucamides, alkyl polyglucosides, oxyalkylenated derivatives of fatty alcohols, alkylamides or alkanolamides, or amphoteric or zwitterionic surface-active agents,
- noncationic bactericides or disinfectants, such as triclosan,
- synthetic cationic polymers,
- polymers for controlling the viscosity of the mixture and/or the stability of the foams formed during use,
- hydrotropic agents,
- hydrating or moisturizing agents or agents for protecting the skin,
- colorants, fragrances, preservatives, divalent salts (in particular magnesium salts), and the like.

The pH of the composition is advantageously between 5 and 9.

Another specific embodiment of the invention is a composition for making easier the exterior cleaning, in particular of the bodywork, of motorized vehicles (automobiles, trucks, buses, trains, planes, and the like).

In this case also, the composition can be a cleaning composition proper or a rinsing composition.

The cleaning composition for motor vehicles advantageously comprises from 0.005 to 10% by weight of polybetaine (B), with respect to the total weight of said composition, and:

- nonionic surface-active agents (in a proportion of 0 to 30%, preferably of 0.1 to 15%, of the formulation),
- amphoteric and/or zwitterionic surface-active agents (in a proportion of 0 to 30%, preferably of 0.01 to 10%, of the formulation),
- cationic surface-active agents (in a proportion of 0 to 30%, preferably of 0.5 to 15%, of the formulation),
- anionic surface-active agents (in a proportion of 0 to 30%, preferably of 0.1 to 15%, of the formulation),
- detergency adjuvants (builders) (in a proportion of 1 to 99%, preferably of 40 to 98%, of the formulation),
- hydrotropic agents,
- fillers, pH modifiers, and the like.

The minimum amount of surface-active agent present in this type of composition is preferably at least 0.5% of the formulation.

The pH of the composition is advantageously between 8 and 13.

The composition of the invention is also particularly suitable for making easier the cleaning of hard surfaces of ceramic type (tiling, bath tubs, bathroom sinks, and the like), in particular for bathrooms.

The cleaning formulation advantageously comprises from 0.02 to 5% by weight of polybetaine (B), with respect to the total weight of said composition, and at least one surface-active agent.

Preference is given, as surface-active agents, to nonionic surface-active agents, in particular the compounds produced by condensation of alkylene oxide groups of hydrophilic nature with a hydrophobic organic compound which can be of aliphatic or alkylaromatic nature.

The length of the hydrophilic chain or of the polyoxyalkylene radical condensed with any hydrophobic group can be readily adjusted in order to obtain a water-soluble compound having the desired degree of hydrophilic/hydrophobic balance (HLB).

The amount of nonionic surface-active agents in the composition of the invention can be from 0 to 30% by weight, preferably from 0 to 20% by weight.

An anionic surfactant can optionally be present in an amount of 0 to 30%, advantageously 0 to 20%, by weight.

It is also possible, but not essential, to add amphoteric, cationic or zwitterionic detergents.

The total amount of surface-active compounds employed in this type of composition is generally between 0.5 and 50%, preferably between 1 and 30%, by weight and more particularly between 2 and 20% by weight, with respect to the total weight of the composition.

Said cleaning composition can also comprise other minor ingredients, such as:

- detergency adjuvants (builders) as mentioned above (in an amount which can be between 0.1 and 25% by weight, with respect to the total weight of the composition),
- a foam modifier as mentioned above, in particular of soap type (in an amount generally of at least 0.005% by weight, preferably of 0.5% to 2% by weight, with respect to the total weight of the composition),
- pH modifiers, colorants, optical brighteners, agents for suspending soiling substances, detergent enzymes, compatible bleaching agents, agents for controlling gel formation, freezing-thawing stabilizers, bactericides, preservatives, solvents, fungicides, insect repellants, hydrotropic agents, fragrances and opacifying or pearlescent agents.

The pH of the composition is advantageously between 2 and 12.

The composition according to the invention is also suitable for making easier the rinsing of shower walls. The aqueous compositions for rinsing shower walls comprise from 0.02% to 5% by weight, advantageously from 0.05 to 1%, of polybetaine (B).

The other main active components of the aqueous compositions for rinsing showers of the present invention are at least one surface-active agent, present in an amount ranging from 0.5 to 5% by weight, and optionally a metal-chelating agent as mentioned above, present in an amount ranging from 0.01 to 5% by weight.

The aqueous compositions for rinsing showers advantageously comprise water with, optionally, a major proportion of at least one lower alcohol and a minor proportion of additives (between approximately 0.1 and approximately 5% by weight, more advantageously between approximately 0.5% and approximately 3% by weight and more preferably still between approximately 1% and approximately 2% by weight).

Some surface-active agents which, can be used in this type of application are disclosed in patents U.S. Pat. Nos. 5,536,452 and 5,587,022, the content of which is incorporated by reference in the present description.

Preferred surfactants are polyethoxylated fatty esters, for example polyethoxylated sorbitan monooleates and polyethoxylated castor oil. Specific examples of such surface-active agents are the condensation products of 20 mol of ethylene oxide and of sorbitan monooleate (sold by Rhodia Inc. under the name Alkamuls PSMO-20® with an HLB of 15.0) and of 30 or 40 mol of ethylene oxide and of castor oil (sold by Rhodia Inc. under the names Alkamuls EL-620® (HLB of 12.0) and EL-719® (HLB of 13.6) respectively). The degree of ethoxylation is preferably sufficient to obtain a surfactant with an HLB of greater than 13.

The pH of the composition is advantageously between 7 and 11.

The composition according to the invention can also be employed for making easier the cleaning of glass-ceramic sheets.

Advantageously, the formulations for cleaning glass-ceramic sheets of the invention comprise:

- 0.01 to 5% by weight of polybetaine (B),
- 0.1 to 1% by weight of a thickener, such as a xanthan gum,
- 10 to 60% by weight of an abrasive agent, such as calcium carbonate or silica;
- 0 to 7% by weight of a solvent, such as butyl diglycol,
- 1 to 10% by weight of a nonionic surface-active agent, and optionally basifying agents or sequestering agents.

The pH of the composition is advantageously between 7 and 12.

As mentioned above, the composition according to the invention can also be employed in the field of industrial cleaning, in particular for making easier the cleaning of reactors.

Advantageously, said compositions comprise:

- from 0.02 to 5% by weight of polybetaine (B),
- from 1 to 50% by weight of alkali metal salts (sodium or potassium phosphates, carbonates, silicates),
- from 1 to 30% by weight of a mixture of surface-active agents, in particular of nonionic surface-active agents, such as ethoxylated fatty alcohols, and anionic surface-active agents, such as laurylbenzenesulfonate,
- from 0 to 30% by weight of a solvent, such as diisobutyl ether.

The pH of such a composition is generally from 8 to 14.

A second subject matter of the invention is the use, in a composition comprising at least one surface-active agent for cleaning or rinsing hard surfaces in an aqueous or aqueous/alcoholic medium, of at least one polybetaine (B)

- carrying, within a pH range from 1 to 14, a permanent anionic overall charge and a permanent cationic overall charge, each individual betaine unit carrying as many permanent anionic charges as permanent cationic charges, and
- exhibiting an absolute weight-average molar mass ($M_w$) ranging from 5000 to 3 000 000 g/mol, preferably from 8000 to 1 000 000 g/mol, very particularly between 10 000 and 500 000 g/mol, as agent which makes it possible to contribute to said surfaces antideposition and/or antiadhesion properties with regard to soiling substances capable of being deposited on said surfaces.

A third subject matter of the invention is a method for improving the properties of compositions comprising at least one surface-active agent for cleaning or rinsing hard surfaces in an aqueous or aqueous/alcoholic medium by addition to said compositions of at least one polybetaine (B)

- carrying, within a pH range from 1 to 14, a permanent anionic overall charge and a permanent cationic overall charge, each individual betaine unit carrying as many permanent anionic charges as permanent cationic charges, and
- exhibiting an absolute weight-average molar mass ($M_w$) ranging from 5000 to 3 000 000 g/mol, preferably from 8000 to 1 000 000 g/mol, very particularly between 10 000 and 500 000 g/mol.

A fourth subject matter of the invention is a method for facilitating the cleaning or rinsing of hard surfaces by bringing said surfaces into contact with a composition in an aqueous or aqueous/alcoholic medium comprising at least one surface-active agent and at least one polybetaine (B), said polybetaine (B) being characterized in that it:

carries, within a pH range from 1 to 14, a permanent anionic overall charge and a permanent cationic overall charge, each individual betaine unit carrying as many permanent anionic charges as permanent cationic charges, and exhibits an absolute weight-average molar mass ($M_w$) ranging from 5000 to 3 000 000 g/mol, preferably from 8000 to 1 000 000 g/mol, very particularly between 10 000 and 500 000 g/mol.

The polybetaine (B) is employed or is present in said composition in an amount which is effective in contributing to said surfaces antideposition and/or antiadhesion properties with regard to soiling substances capable of being deposited on said surfaces.

The nature and the amounts of the polybetaine (B) present or employed in said composition, as well as the other additives and various forms of application of said composition, have already been mentioned above.

The following examples are given by way of illustration.

The following homopolysulfobetaines B1 to B8 and the following copolysulfobetaines C1 to C7 are prepared in the laboratory according to a solution radical polymerization method well known to a person skilled in the art, the performances of which homopolysulfobetaines and copolysulfobetaines will be tested in the examples below.

B1 Poly(sulfopropyldimethylammonioethyl methacrylate), “poly(SPE)”, with an absolute weight-average molar mass ($M_w$) of 35 000 g/mol B2 Poly(sulfopropyldimethylammonioethyl methacrylate) with an absolute weight-average molar mass ($M_w$) of 55 000 g/mol B3 Poly(sulfopropyldimethylammonioethyl methacrylate) with an absolute weight-average molar mass ($M_w$) of 110 000 g/mol B4 Poly(sulfopropyldimethylammonioethyl methacrylate) with an absolute weight-average molar mass ($M_w$) of 450 000 g/mol B5 Poly(sulfopropyldimethylammonioethyl methacrylate) with an absolute weight-average molar mass ($M_w$) of 1 200 000 g/mol B6 Poly(sulfopropyldimethylammonioethyl methacrylate) with an absolute weight-average molar mass ($M_w$) of 1 800 000 g/mol B7 Poly(sulfopropyldimethylammoniopropylmethacrylamide), “poly(SPP)”, with an absolute weight-average molar mass ($M_w$) of 55 000 g/mol B8 Poly(sulfohydroxypropyldimethylammoniopropylmethacrylamide), “poly(SHPP)”, with an absolute weight-average molar mass ($M_w$) of 60 000 g/mol C1 Poly(sulfopropyldimethylammonioethyl methacrylate-co-methacrylic acid), “poly(SPE/MAA)”, with an absolute weight-average molar mass ($M_w$) of 50 000 g/mol, exhibiting an SPE/MAA molar ratio of 95/5

C2 Poly(sulfopropyldimethylammonioethyl methacrylate-co-methacrylic acid) with an absolute weight-average molar mass ($M_w$) of 50 000 g/mol, exhibiting an SPE/MAA molar ratio of 85/15

C3 Poly(sulfopropyldimethylammonioethyl methacrylate-co-methacrylic acid) with an absolute weight-average molar mass ($M_w$) of 50 000 g/mol, exhibiting an SPE/MAA molar ratio of 66/34

C4 Poly(sulfopropyldimethylammonioethyl methacrylate-co-methacrylic acid) with an absolute weight-average molar mass ($M_w$) of 50 000 g/mol, exhibiting an SPE/MAA molar ratio of 60/40

C5 Poly(sulfopropyldimethylammonioethyl methacrylate-co-methacrylic acid) with an absolute weight-average molar mass ($M_w$) of 50 000 g/mol, exhibiting an SPE/MAA molar ratio of 49/51

C6 Poly(sulfopropyldimethylammonioethyl methacrylate-co-methacrylic acid) with an absolute weight-average molar mass ($M_w$) of 50 000 g/mol, exhibiting an SPE/MAA molar ratio of 40/60

C7 Poly(sulfopropyldimethylammonioethyl methacrylate-co-methacrylic acid) with an absolute weight-average molar mass ($M_w$) of 50 000 g/mol, exhibiting an SPE/MAA molar ratio of 25/75

The molar masses mentioned are absolute weight-average molar masses measured by aqueous gel permeation chromatography GPC by MALLS light scattering, according to the following conditions:

| | |
|---|---|
| Eluent: | 18 MΩ Millipore water, 1M $NH_4NO_3$, 1/10 000 $NaN_3$ |
| Flow rate: | 1 ml/min |
| Volume injected: | 100 μl |
| Calibration: | None, the weight is established by MALLS |
| Columns: | 2 GPC columns (SB806MHQ Shodex OH Pack 30 cm, 5 μm) |
| Detectors: | Refractometer: RI Waters 410<br>DLS: MALLS (multi-angle laser light scattering) light scattering, Wyatt, laser He 633 nm |

PRELIMINARY EXAMPLE 1

Intrinsic Properties with Regard to Antiadhesion of Soiling Substance of the Betaine Polymers or Copolymers B1 to B8 and C1 to C7 (Visual Tests)

The betaine polymers B1 to B8 tested are respectively employed in the form of a solution at a concentration of 200 mg/l in a water/ethanol mixture comprising 5% by volume of ethanol (this in order to facilitate the drying of the solution deposited on the surface to be treated); the solution is brought to pH 3 by addition of hydrochloric acid.

The intrinsic performances of the betaine polymers B1 to B8 according to the invention are tested visually and are compared with those obtained in the absence of betaine polymer B1 to B8, in the presence of a zwitterionic surface-active agent (ZwSurf) of cocamidopropyl hydroxysultaine type (Mirataine CBS from Rhodia), employed in the form of a solution at a concentration of 200 mg/l in a water/ethanol mixture comprising 5% by volume of ethanol; the solution is brought to pH 3 by addition of hydrochloric acid Test Use is made of a black-colored ceramic sheet with dimensions of 25 cm×25 cm cleaned beforehand using ethanol, the surface of which is divided into 10 equal parallel fractions F, F', F1, F2, F3, F4, F5, F6, F7 and F8. The procedure is as follows 1. Treatment The first fraction, F, of the sheet is left as is.

2.5 mg/$m^2$ of zwitterionic surfactant (solution in the water/ethanol mixture, of pH 3) are deposited over the whole of the second fraction, F', using a film drawer.

2.5 mg/$m^2$ of polymer B1 to B8 (solutions in the water/ethanol mixture, of pH 3) are respectively deposited over the whole of the fractions F1 to F8 using a film drawer.

2. Deposition of Soiling Substance 15 g of following model soiling substance are deposited over the whole of the rinsed sheet and are left to dry in the air for 24 hours.

The white-colored model soiling substance employed is composed of

75% by weight of water
10% by weight of cellulose
7.5% of inorganic salts (calcium phosphate, iron phosphate)
5% by weight of cholesterol
2.5% by weight of edible oil (olive oil, castor oil)

3. Rinsing

The soiled sheet is subsequently rinsed using one liter of hard municipal water and is left to dry.

The sheet is analyzed visually by a group of 20 testers.

The results are recorded as follows

1: very dirty surface
5: clean surface

The test described above is also carried out while replacing the polymers B1 to B8 with the copolymers C1 to C7.

The combined results are given below:

| Treatment using | ($M_w$) in g/mol | Performance |
|---|---|---|
| None (reference) | — | 1 |
| ZwSurf | — | 2.1 |
| B1 poly(SPE) | 35 000 | 4.9 |
| B2 poly(SPE) | 55 500 | 4.6 |
| B3 poly(SPE) | 110 000 | 4.2 |
| B4 poly(SPE) | 450 000 | 3.9 |
| B5 poly(SPE) | 1 200 000 | 2.2 |
| B6 poly(SPE) | 1 800 000 | 2.1 |
| B7 poly(SPP) | 55 000 | 4.7 |
| B8 Poly(SHPP) | 60 000 | 4.6 |
| C1 poly(SPE/MAA) 95/5 | 50 000 | 4.6 |
| C2 poly(SPE/MAA) 85/15 | 50 000 | 4.5 |
| C3 poly(SPE/MAA) 66/34 | 50 000 | 4.4 |
| C4 poly(SPE/MAA) 60/40 | 50 000 | 4.4 |
| C5 poly(SPE/MAA) 49/51 | 50 000 | 4.2 |
| C6 poly(SPE/MAA) 40/60 | 50 000 | 4.2 |
| C7 poly(SPE/MAA) 25/75 | 50 000 | 4.1 |

It is found that the betaine polymers B1 to B8 and C1 to C7 facilitate the removal of the soiling substances. The polymers B1 to B4, B7 and B8, and C1 to C7, with an $M_w$ of less than 500 000 g/mol, are very effective, very particularly those with an $M_w$ of less than 150 000 g/mol. The SPE/MAA molar ratio of the copolymers C1 to C7 has only a slight impact in this test.

PRELIMINARY EXAMPLE 2

Intrinsic Properties with Regard to Persistence (after 200 Rinsing Operations) and Antiadhesion of Soiling Substance of the Betaine Polymers B1, B5, B7, C1, C2, C4 and C6 (Visual Tests)

The betaine polymers B1, B5, B7, C1, C2, C4 and C6 tested are employed in the form of solutions at a concentration of 200 mg/l in a water/ethanol mixture comprising 5% by volume of ethanol (this in order to facilitate the drying of the solution deposited on the surface to be treated); the solutions are brought to pH 3 by addition of hydrochloric acid.

The intrinsic performance of the betaine polymers B1, B5, B7, C1, C2, C4 and C6 according to the invention are tested visually and are compared with those obtained in the absence of betaine polymer B1, B5, B7, C1, C2, C4 or C6 in the presence of a zwitterionic surface-active agent (ZwSurf) of cocamidopropyl hydroxysultaine type (Mirataine CBS from Rhodia), employed in the form of a solution at a concentration of 200 mg/l in a water/ethanol mixture comprising 5% by volume of ethanol; the solution is brought to pH 3 by addition of hydrochloric acid Test Use is made of a black-colored ceramic sheet with dimensions of 20 cm×20 cm cleaned beforehand using ethanol, the surface of which is divided into 3 equal parallel fractions.

The procedure is as follows

1. Treatment

The first fraction of the sheet is left as is.

2.5 $mg/m^2$ of zwitterionic surfactant (solution in the water/ethanol mixture, of pH 3) are deposited over the whole of the second fraction using a film drawer).

2.5 $mg/m^2$ of polymer B1, B5, B7, C1, C2, C4 or C6 (solution in the water/ethanol mixture, of pH 3) are deposited over the whole of the third fraction using a film drawer.

2. Rinsing

The treated sheet is subjected to 200 rinsing cycles using 200×1 liter of water.

3. Deposition of Soiling Substance 15 g of following model soiling substance are deposited over the whole of the rinsed sheet and are left to dry in the air for 24 hours.

The white-colored model soiling substance employed is composed of

75% by weight of water
10% by weight of cellulose
7.5% of inorganic salts (calcium phosphate, iron phosphate)
5% by weight of cholesterol
2.5% by weight of edible oil (olive oil, castor oil).

4. Final Rinsing

The soiled sheet is subsequently rinsed using one liter of hard municipal water and is left to dry in the air for 30 minutes.

The sheet is analyzed visually by a group of 20 testers.

The results are recorded as follows

1: very dirty surface
5: clean surface

| Treatment using | (Mw) in g/mol | Performance |
|---|---|---|
| None (reference) | — | 1 |
| ZwSurf | — | 1 |
| B1 | 35 000 | 4.1 |
| B5 | 1 200 000 | 1.9 |
| B7 | 55 000 | 4.2 |
| C1 poly(SPE/MAA) 95/5 | 50 000 | 3.9 |
| C2 poly(SPE/MAA) 85/15 | 50 000 | 3.8 |
| C4 poly(SPE/MAA) 60/40 | 50 000 | 2.5 |
| C6 poly(SPE/MAA) 40/60 | 50 000 | 1.2 |

It is found that the betaine polymers, very particularly the polymers B1, B7, C1 and C2, in contrast to a simple zwitterionic surface-active agent, remain on the surface for at least 200 rinsing cycles; the polymers of the invention endure on the surface.

The polymers do not leave at the same time as the soiling substance; without this being related to any one mechanism, it is assumed that the mechanism of antiadhesion of the soiling substance is not “sacrificial”.

Example 1

Compatibility of the Polymer B1 and of the Copolymer C1 with Surface-Active Agents which are Conventional in Detergency 4×6 detergent solutions are prepared respectively comprising 0 mg/l, 50 mg/l, 100 mg/l and 200 mg/l of polymer B1 or C1

10 g/l and 50 g/l of one of the following surfactants:

- nonionic, Rhodasurf ID/060 from Rhodia
- anionic, LaurylAlkylBenzeneSulfonate (Nansa from Rhodia),
- cationic, Rhodaquat RP 50 from Rhodia, the pH of which is adjusted to 3 by addition of 0.01 molar sulfuric acid.

The transmission of the 24 solutions is measured using a photometer. The transmission of the 24 solutions is identical and comparable with that of a solution of water at pH 3.

The polymers B1 and C1 are thus compatible with all the types of surfactants commonly used in detergency; they can thus be formulated in any type of commercial formulation without the risk of bringing about phase separation or instability over time.

Each aqueous solution is sprayed over a black ceramic tile and is then wiped with a commercial cellulose dust cloth. The model soiling substance employed is composed of

- 75% by weight of water
- 10% by weight of cellulose
- 5% by weight of cholesterol
- 2.5% by weight of edible oil (olive oil, castor oil)
- 7.5% of inorganic salts (calcium phosphate, iron phosphate).

It is applied to the surface thus prepared and is left to dry for 24 hours. Faucet water is subsequently sprayed over the surface.

The percentage of the soiling substance deposited which has not remained on the surface is evaluated by image analysis.

The results obtained are given in the following table:

| Percentage of the soiling substance deposited which has not remained on the surface | | | | | | |
|---|---|---|---|---|---|---|
| | Surface-active agent | | | | | |
| | Nonionic | | Anionic | | Cationic | |
| mg/l | 10 g/l | 50 g/l | 10 g/l | 50 g/l | 10 g/l | 50 g/l |
| B1 | | | | | | |
| 0 | 20 | 15 | 10 | 18 | 20 | 22 |
| 50 | 60 | 87 | 25 | 27 | 63 | 80 |
| 100 | 95 | 89 | 55 | 30 | 81 | 82 |
| 200 | 100 | 99 | 65 | 65 | 90 | 84 |
| C1 | | | | | | |
| 0 | 20 | 15 | 10 | 18 | 20 | 22 |
| 50 | 60 | 85 | 23 | 25 | 60 | 78 |
| 100 | 95 | 88 | 53 | 30 | 80 | 79 |
| 200 | 100 | 100 | 60 | 58 | 88 | 82 |

It is found that a detergent composition comprising the polymer B1 or C1 according to the invention facilitates the removal of soiling substances of toilet type on ceramics.

The polymer B1 or C1 is particularly effective in the presence of a nonionic or cationic surface-active agent, at pH 3.

Example 2

Formulations for Making it Easier to Clean Windows

The compositions of four cleaning formulations (including two comparative formulations, A and B) used for cleaning windows are reported in the table below.

| | Formulation | | | |
|---|---|---|---|---|
| Components | A comp. (by weight) | B comp. (by weight) | C (by weight) | D (by weight) |
| Isopropyl alcohol | 7 | 7 | 7 | 7 |
| Alkylpolyglucoside | 0 | 0.3 | 0 | 0.3 |
| Sodium dodecylbenzenesulfonate | 0.4 | 0 | 0.4 | 0 |
| Ammonium hydroxide | 0.3 | 0.3 | 0.3 | 0.3 |
| Dipropylene glycol monomethyl ether | 3 | 3 | 3 | 3 |
| Polymer B2 | 0 | 0 | 0.05 | 0.05 |
| Water | q.s. for 100 | q.s. for 100 | q.s. for 100 | q.s. for 100 |
| pH of the formulation | 7 | 7 | 7 | 7 |
| Immediate appearance | 5 | 5 | 5 | 5 |
| Appearance after | | | | |
| 1 week | 4 | 4 | 5 | 5 |
| 2 weeks | 3 | 4 | 5 | 5 |
| 4 weeks | 2 | 3 | 5 | 5 |
| 6 weeks | 1 | 3 | 5 | 4 |
| 8 weeks | 1 | 2 | 4 | 4 |

Four exterior windows with an area of 1 $m^2$ situated side by side are treated as follows with the formulations A, B, C and D respectively.

Each formulation is sprayed over the respective window in a proportion of 5 ml per $m^2$ of surface area and is then directly wiped with a commercial cellulose dust cloth.

After treatment, the appearance of the window, exposed to the effects of the weather for 8 weeks, is recorded over time.

A panel of observers records, over a scale of 1 to 5, the cleanness of the windows (possible marks, sparkle, carbon residues).

A grade of 1 corresponds to a very dirty window and 5 corresponds to the initial appearance, immediately after cleaning.

This test clearly demonstrates that the polybetaine B2 contributes a soil-release property which persists over at least 6 weeks.

Example 3

Cleaning Formulations for Linoleum Floors

The formulations tested appear in the following table:

| | Formulations | |
|---|---|---|
| Components | A (by weight) | B (by weight) |
| Alkyl ether sulfate (2 EO) | 7 | 7 |
| Alkyl polyglucoside | 3 | 3 |
| Glycol ether | 1 | 1 |
| Citrate | 1 | 1 |
| Polymer B7 | 0 | 1 |

-continued

| | Formulations | |
|---|---|---|
| Components | A (by weight) | B (by weight) |
| Water | q.s. for 100 | q.s. for 100 |
| Drying time | 180 seconds | 120 seconds |

The formulations A and B are diluted before use in a proportion of 10 g of formulation in 1 liter of water. Half the floor is treated with the formulation A and the other half is treated with the formulation B comprising the additive.

The floor is made of linoleum.

The user records at what rate the floor becomes dry by passing his hand over the latter.

Example A is given by way of comparison. The results for drying rate of the formulations A and B show that the polymer introduces into the formulation a marked improvement in the drying rate for the consumer.

With the formulation comprising the additive, the drying time is reduced by approximately 30%.

The user also finds that the polymer B7 contributes properties of shininess during drying.

Furthermore, the part of the floor treated with the formulation B is markedly less slippery than the part treated with the formulation A, thus conferring slip-resistance properties on the treated surface.

After two weeks of use, the operator is asked to clean the floor with the formulation A.

It is apparent that the removal of soiling substances of soot and carbon black type is facilitated on the part of the floor which has been treated beforehand with the formulation B. Thus, the polymer B7 confers antiadhesion properties with regard to soiling substance on the surfaces treated.

Example 4

Detergent Formulations for Automatic Dishwashers

Glasses are placed in an automatic dishwasher and the powder detergent formulation, the composition of which is given in the following table, is placed in the reservoir provided for this purpose with a dosage of 32 g.

No rinsing liquid is used in this test.

These glasses are washed with the "normal" program, which gives a maximum washing temperature of 65° C.

During the washing cycle, an open container holding a mixture of egg, oil, cream, cheese and ketchup is simultaneously introduced into the dishwasher.

At the end of the washing, the dishwasher is kept closed for 3 hours.

After the washing cycle, the performance of the detergent composition is measured in terms of antiredeposition of soiling substances on the surface of the glass (giving rise to a white deposit/veil) and the hydrophilicity of the surfaces thus treated is also measured.

To do this, a solution of water is sprayed over the glass and the time which the film of water takes to drain (to flow homogeneously) or to remain on the surface is evaluated visually.

| | Formulation | | | |
|---|---|---|---|---|
| Constituents | A (by weight) | B (by weight) | D (by weight) | E (by weight) |
| Sodium tripolyphosphate | 0 | 45 | 0 | 45 |
| Sodium carbonate | 30 | 20 | 30 | 20 |
| Sodium disilicate | 15 | 10 | 15 | 10 |
| Sodium citrate | 20 | 0 | 20 | 0 |
| Sodium sulfate | 12 | 8 | 14 | 10 |
| Sokalan CP5 from BASF (Sodium maleate and acrylate copolymer) | 6 | 0 | 6 | 0 |
| Acusol 587 D | 2 | 2 | 2 | 2 |
| Plurafac LF 403 | 2 | 2 | 2 | 2 |
| Bleaching system (perborate.1$H_2O$ + TAED**) | 10 | 10 | 10 | 10 |
| Other additives (enzymes, fragrance, and the like) | 3 | 3 | 3 | 3 |
| Polymer B1, B7 or C3 | 2 | 2 | 0 | 0 |
| pH | 10.5 | 10.4 | 10.5 | 10.4 |
| "Soiled" appearance | | | | |
| without polymer | | | 2 | 3 |
| with B1 | 4.5 | 5 | | |
| with B7 | 4.2 | 4.4 | | |
| with C3 | 4 | 4.5 | | |
| Draining of water on the surface | Yes | Yes | Yes | No |

**tetraacetylethylenediamine

Furthermore, after washing, the appearance of the glasses is evaluated.

The grading "1" corresponds to a very dirty glass.

The grading "5" corresponds to a "clean" glass.

The results show that, during the washing cycle, the polymer B1 or B7 or the copolymer C3 brings the particles of soiling substance into suspension and prevents their deposition on the surface.

Example 5

Detergent Formulations for Automatic Dishwashers

Two comparative tests are carried out between two commercial cleaning formulations for automatic dishwashers (formulations D and E) and two similar formulations (A and B) comprising the polymer B1 or C3.

The compositions of the formulations A, B, D and E are given in the table of the preceding Example 4.

1st Comparative Test

Four automatic dishwashers are available.

A dish made of glass of Pyrex® type and 22 g of a detergent formulation chosen from the formulations A, B, D and E respectively are placed in each.

The dishes are prewashed with the "normal" program at 55° C.

The dishes P thus treated are denoted as follows:

$P_A$ treated with the formulation A $P_B$ treated with the formulation B $P_D$ treated with the formulation D $P_E$ treated with the formulation E A preparation of "gratin" type is subsequently cooked in each of the dishes.

After having been emptied of their contents, the dishes $P_A$ and $P_D$ are washed (1 dish per dishwasher) for 3 consecutive cycles using the formulation D (without polybetaine).

After having been emptied of their contents, the dishes $P_B$ and $P_E$ are washed (1 dish per dishwasher) for 3 consecutive cycles using the formulation E (without polybetaine).

After washing, the dishes are removed from the dishwashers and their appearance is compared.

| Removal of the soiling substances (%) | Formulation A (by weight) | B (by weight) | D (by weight) | E (by weight) |
|---|---|---|---|---|
| Without polybetaine | | | 67 | 72 |
| With B1 | 79 | 81 | | |
| With C3 | 75 | 78 | | |

It is found that the soiling substances adhere less to the dishes prewashed with the formulation A or B.

2nd Comparative Test

Four automatic dishwashers are available.

A batch of plates and 22 g of a detergent formulation chosen from the formulations A, B, D and E respectively are placed in each.

The batches are prewashed with the "normal" program at 55° C.

The batches L thus treated are denoted as follows:

$L_A$ treated with the formulation A $L_B$ treated with the formulation B $L_D$ treated with the formulation D $L_E$ treated with the formulation E A model soiling substance comprising egg, beef flesh, vegetable fat and proteins is deposited on the 4 batches of prewashed plates. Drying is allowed to take place at 60° C. for 1 hour.

The batches $L_A$ and $L_D$ are washed (1 batch per dishwasher) for 3 consecutive cycles using the formulation D (without polybetaine).

The batches $L_B$ and $L_E$ are washed (1 batch per dishwasher) for 3 consecutive cycles using the formulation E (without polybetaine).

After washing, the batches of plates are removed from the dishwashers and their appearance is compared.

| Removal of the soiling substances (%) | Formulation A (by weight) | B (by weight) | D (by weight) | E (by weight) |
|---|---|---|---|---|
| Without polybetaine | | | 55 | 65 |
| With B1 | 64 | 79 | | |
| With C3 | 61 | 78 | | |

The polymers B1 and C3 thus improve the ability of the formulations to prevent the adhesion of soiling substances in automatic dishwashers.

Example 6

Antiredeposition of Calcium Carbonate and Phosphates on Articles Washed in Dishwashers The polymer B1 or the copolymer C3 is introduced into an automatic dishwasher formulation which may or may not comprise sodium tripolyphosphate.

Filming (formation of a white veil by deposition of inorganic calcium salts on the surface) is brought about by the addition of 2 grams of orthophosphate ($NaHPO_4$) at each cycle start in the dishwasher.

The number of washing cycles (with a 35° TH water) necessary for the appearance of a white veil on the glasses is measured.

| Constituents | Formulation A (by weight) | B (by weight) | D (by weight) | E (by weight) |
|---|---|---|---|---|
| Sodium tripolyphosphate | 0 | 45 | 0 | 45 |
| Sodium carbonate | 30 | 20 | 30 | 20 |
| Sodium disilicate | 15 | 10 | 15 | 10 |
| Sodium citrate | 20 | 0 | 20 | 0 |
| Sodium sulphate | 12 | 8 | 14 | 10 |
| Sokalan CP5 from BASF (sodium acrylate and maleate copolymer) | 6 | 0 | 6 | 0 |
| Plurafac LF 403 | 2 | 2 | 2 | 2 |
| Bleaching system (perborate.$1H_2O$ + TAED**) | 10 | 10 | 10 | 10 |
| Other additives (enzymes, fragrance, and the like) | 3 | 3 | 3 | 3 |
| Polymer B1 or C3 | | 3 | 0 | 0 |
| pH | 10.5 | 10.4 | 10.5 | 10.4 |
| Number of cycles | | | | |
| without polymer | | | 4 | 3 |
| with B1 | >10 | 9 | | |
| with C3 | >10 | 8 | | |

**ethylenediaminetetraacetate

These results show that the polymer B1 or C3 prevents (inhibits) the deposition of calcium carbonate and phosphate on the dishes.

This type of polymer is recommended for use in dishwasher compositions of 2-in-1 type (washing and rinsing) or even of 3-in-1 type (softening, washing and rinsing).

Example 7

Rinsing Formulations for Automatic Dishwashers

The washing operation described in Example 6 with the formulation D (without sodium tripolyphosphate and without polymer B1) is repeated.

This operation is followed by a rinsing stage carried out with the rinsing formulations F1 to F3 given in the following table:

| Constituents | Formulation F1 (by weight) | F2 (by weight) | F3 (by weight) |
|---|---|---|---|
| Nonionic surfactant C13-3PO-7EO (EO/PO linear fatty alcohol) | 12 | 6 | 0 |
| Citric acid | 3 | 3 | 3 |
| Polymer B3 | 0 | 1 | 2 |
| Water | q.s. for 100 | q.s. for 100 | q.s. for 100 |
| pH | 5 | 5 | 5 |
| Contact angle | 25 | 20 | 15 |

The contact angle results obtained with regard to the formulations F2 and F3 show that the polymer B3 introduces into the formulation a hydrophilization of the glass surface in dishwashers which is not encountered with the formulation F1.

The polymer of the invention makes it possible advantageously to substitute the amount of nonionic surfactant by a polymer which contributes sparkling properties to the utensils treated (in particular with regard to glasses).

Example 8

Formulation for Washing Dishes by Hand

Two comparative tests are carried out between two commercial formulations for cleaning dishes by hand (formulations A and C) and two formulations (B and D) comprising the polymer B2.

| | Formulation | | | |
|---|---|---|---|---|
| Constituents | A (by weight) % | B (by weight) % | C (by weight) % | D (by weight) % |
| Sodium ($C_{14}$)alkylsulfonate | 20 | 20 | 13 | 13 |
| Alkyl ether sulphate | 5 | 5 | 0 | 0 |
| Alkyl amidobetaine | 2 | 2 | 1 | 1 |
| Alkyl polyglucoside | 0 | 0 | 3.2 | 3.2 |
| Xylenesulfonate | 3.2 | 3.2 | 1.6 | 1.6 |
| Polymer B2 | 0 | 4 | 0 | 3 |
| Water | q.s. for 100 | q.s. for 100 | q.s. for 100 | q.s. for 100 |
| pH | 7 | 7 | 7 | 7 |

1st Comparative Test

A dish made of glass of Pyrex® type $P_A$ is prewashed in a first sink by hand with the formulation A diluted 1000-fold in water.

In the same way, a dish made of glass of Pyrex® type $P_B$ is prewashed in a second sink by hand with the formulation B (comprising the betaine polymer B2) diluted 1000-fold in water.

The dishes thus treated with the formulations A and B are subsequently dried in the open air.

A preparation of "gratin" type is cooked in each of the dishes at 180° C. for one hour. They are subsequently emptied of their contents.

The dish $P_A$ is left to soak for 1 hour in a first sink filled with the formulation A (without polybetaine) diluted a thousand fold in water.

The dish $P_B$ is left to soak for 1 hour in a second sink filled with the formulation A (without polybetaine) diluted a thousand fold in water.

After soaking for one hour, the dishes are removed from the sinks and their appearance is compared.

It is found that the soiling substance adheres much less to the dish $P_B$ pretreated with the formulation B than to the dish $P_A$.

2nd Comparative Test

Two batches of 30 plates each are soiled with a model soiling substance comprising egg, beef flesh, vegetable fat and proteins. Drying is allowed to take place at 60° C. for 1 hour.

The first batch of 30 plates (referred to as "Batch C") is washed with the formulation C (without polybetaine) in 2 liters of faucet water; the number of plates of Batch C which can be cleaned is counted; the amount counted is 15 plates.

The second batch of 30 plates (referred to as "Batch D") is washed with the formulation D (with polybetaine) in 2 liters of faucet water; the number of plates of Batch D which can be cleaned is counted; the amount counted is 22 plates.

The polymer B2 thus improves the cleaning ability of the formulations for washing dishes by hand.

Example 9

Cleaning Formulations for Bathrooms

The formulations employed are given in the following table:

| | Formulation | |
|---|---|---|
| Constituents | A (by weight) | B (by weight |
| Sodium ($C_{12}$) alkylsulfonate | 3 | 3 |
| Ethoxylated (6 EO) $C_{12}$ fatty alcohol | 5 | 5 |
| Ethanol | 4 | 4 |
| Polymer B2 | 0 | 0.5 |
| Water | q.s. for 100 | q.s. for 100 |
| pH | 7 | 7 |
| Performance | | |
| Bath tub | 6 days | 10 days |
| Wall tiling | 4 days | 8 days |

The formulation A (without polybetaine) is sprayed over half the interior surface of a bath tub made of polyester reinforced by glass fibers and over half of a wall surface made of tiling.

The formulation B (with polybetaine) is sprayed over the other half of the interior surface of the bath tub made of polyester reinforced by glass fibers and over the other half of the wall surface made of tiling.

The surfaces are subsequently rinsed with faucet water.

The user is then requested to record after how many days of use of the bath tub he feels the need to clean "the white marks" which appear either on the wall tiling or on the bath tub.

A significant effect of the addition of polybetaine on preventing the appearance of marks on pretreated surfaces is found.

Example 10

Treatment of Toilet Bowls 0.05 part by weight of polybetaine B1, B7, B8 or C1 is added to 100 parts by weight of a commercial cleaning formulation for toilet bowls based on

| | |
|---|---|
| nonionic surface-active agents | 0.5% by weight |
| anionic surface-active agents | 0.5% by weight |
| citric acid | 8% by weight |
| water | 91% by weight |

Half of the surface of the bowl is treated using the commercial formulation and the other half is treated using the commercial formulation to which polybetaine has been added.

The bowl is rinsed using the flow of the flush of water.

The model soiling substance of Preliminary Example 1 is deposited over the whole of the bowl using a soft brush and is left to dry for 20 minutes before a further flow of the flush of water.

This deposition of soiling substance/drying/flow of the flush of water stage ("cycle") is repeated; the number of cycles at the end of which a phenomenon of accumulation of soiling substance (soil buildup) is observed is recorded.

The results obtained are as follows:

| Formulation | Number of cycles before soil buildup |
|---|---|
| Commercial | 3 |
| Commercial + polybetaine B1 | 19 |
| Commercial + polybetaine B7 | 18 |
| Commercial + polybetaine B8 | 17 |
| Commercial + polybetaine C1 | 17 |

The polymer of the invention thus improves the removal and the antiadhesion of soiling substances on toilet bowls.

Example 11

Composition for the Persistent Treatment of Automobile Bodywork

The polymer B7 of the invention is impregnated onto sodium carbonate and the following two formulations are prepared:

| Components | Formulation | Formulation |
|---|---|---|
| STPP | 60 | 60 |
| Sodium carbonate | 35 | 35 |
| Nonionic surfactant (Rhodoclean MSC) | 2 | 2 |
| Polymer B7 | 0 | 3 |

The powder is subsequently diluted 200-fold (i.e., 10 g of powder are dissolved in 2 l of water) before being applied to the automobile using a high-pressure jet of Kärcher type. Half the automobile is treated with the reference formulation and the other half with the formulation to which polymer B7 has been added.

After washing, the appearance of the two sides of the automobile is similar. After using for 1 month, the automobile is rinsed with detergent-free water. The treated and untreated appearances are then compared.

It is clearly apparent that the film of dust has been removed from the side of the part treated with the polymer of the invention.

Example 12

Improved Cleaning of Kitchen Surfaces

Preparation of the Soiling Substance 60 g of sunflower oil 10 g of olive oil and 20 g of iron oxide pigments are mixed with stirring in a plastic beaker at ambient temperature for 30 minutes.

A crosslinking agent is prepared in another beaker by mixing 45 g of isooctane and 1 g of cobalt naphthenate for 30 minutes.

The final soiling substance which will be applied to the surface is obtained by pouring 20.0 g of the crosslinking agent into the 90 g of soiling substance.

The mixture is stirred for 5 hours at ambient temperature before application.

Materials

Several series of 8 squares made of white Formica®, each of 5 cm×5 cm per side and with a thickness of 1.3 cm, are used. Each square is cleaned beforehand with 0.1 ml of ethanol and is left to dry for at least 30 minutes.

Pretreatment Formulation and Pretreatment Method

A solution comprising 0.4% of polymer B7, 0.5% of cationic surfactant, 4% of ethylene glycol monobutyl ether, 5% of isopropanol and 1% of trimethylamine is prepared.

0.1 ml of pretreatment solution is sprayed over the surface of each square to be evaluated; drying is allowed to take place at ambient temperature for 5 minutes. A sponge moistened with water is passed three times over each surface in order to ensure that the pretreatment is homogeneous.

The squares are subsequently allowed to dry for 3 hours.

Final Cleaning Formulation

A formulation comprising 0.5% of cationic surfactant, 4% of ethylene glycol monobutyl ether, 5% of isopropanol and 1% of trimethylamine is prepared.

Equipment

"Scraper"

It is a guiding device in which the 8 squares of each series are aligned horizontally.

The four squares of the center are numbered 3, 4, 5, 6; the squares placed at the ends are numbered 1 and 2, on the one hand, and 7 and 8, on the other hand.

A metal rod is placed above the squares in order to make possible the passage of a cellulose sponge cut to the size of 4 cm×4 cm from one side to the other of the squares; the sponge is capable of being applied to the squares at a constant pressure using a screw and of moving from one side to the other of squares 1 to 8 along the guiding device.

Paint Roller

For applying the soiling substance to the squares.

Test

1) Precleaning

Each of the 8 squares is cleaned beforehand with 0.1 ml of ethanol and is left to dry for at least 30 minutes.

2) Pretreatment

Four of the 8 squares are subsequently pretreated according to the method given above.

3) Alignment in the Scraper

The 8 squares are aligned in the scraper, the four pretreated squares (numbered 3, 4, 5 and 6) being situated at the center of the scraper, the nonpretreated squares (numbered 1 and 2, on the one hand, and 7 and 8, on the other hand) being situated at the ends and being used only to prevent "edge effects".

4) Deposition of the Soiling Substance

Deposition of a "Light" Soiling Substance

A drop of soiling substance is applied to the squares 3 and 5; this soiling substance is subsequently distributed evenly over the squares 3 to 6 by passage of the paint roller.

The 8 squares are subsequently placed in an oven at 250° C. and 30% relative humidity for 24 hours.

Deposition of a "Difficult" Soiling Substance

A drop of soiling substance is applied to the squares 3 and 5; this soiling substance is subsequently distributed evenly over the squares 3 to 6 by passage of the paint roller.

A drop of soiling substance is applied to the squares 4 and 6; this soiling substance is subsequently distributed evenly over the squares 3 to 6 by passage of the paint roller.

The 8 squares are subsequently placed in an oven at 250° C. and 50% relative humidity for 24 hours.

5) Final Cleaning 0.1 ml×2 of final cleaning formulation are applied on two occasions using the cellulose sponge to the pretreated tiles 3 to 6.

The cellulose sponge is subsequently moved from one side to another of squares 1 to 8 along the guiding device. One sponge pass is counted when the sponge has passed from square 1 to square 8 or vice versa.

Five to-and-fro movements (10 passes) are carried out.

The removal of the soiling substances is subsequently evaluated visually.

A grading of:

0 corresponds to no removal of soiling substance 5 corresponds to complete removal.

The test is repeated 3 times, the squares to be evaluated (those numbered from 3 to 6) being changed.

The mean grades obtained are as follows: for the reference (i.e. squares treated solely with the formulation not comprising the polymer B7)

| Formulation | "Light" soiling substance | "Difficult" soiling substance |
|---|---|---|
| Reference | 1.3 | 0 |
| Polymer B7 | 3.5 | 2 |

What is claimed is:

1. A process of cleaning or rinsing a hard surface, comprising the step of treating a hard surface with a composition comprising in an aqueous or aqueous/alcoholic medium at least one surfactant and at least one polybetaine (B) comprising:

a homopolymer comprising betaine units comprising (-SPE-), (-SPP-), (-SHPE-), or (-SHPP-);

a copolymer comprising at least two different hetaine units of formulae (-SPE-), (-SPP-) (-SHPE-) or (-SHPP-);

a copolymer comprising identical or different betaine units of formulae (-SPE-), (-SPP-), (-SHPE-) or (-SHPP-) and methacrylic acid units, wherein the amount of methacrylic acid units is less than 50 mol % of said copolymers; or mixtures thereof.

2. The process of claim 1, wherein the polyhetaine (B) comprises up to 80% by weight of monomer units which are nonionic, noniogenic, anionic or potentially anionic at the pH of the composition or at the pH of use of the composition.

3. The process of claim 1, wherein the polybetaine (B) comprises up to 90 mol % of monomer units which are nonionic, noniogenic, anionic or potentially anionic at the pH of the composition or at the pH of use of the composition.

4. The process of claim 1, wherein the polyhetaine (B) does not comprise monomer units other than betaine units carrying as many permanent anionic charges as permanent cationic charges at a pH ranging from 1 to 14, or wherein the polybetaine (B) does not comprise monomer units other than betaine units carrying as many permanent anionic charges as permanent cationic charges at a pH ranging from 1 to 14, except that the polybetaine (B) comprises other potentially anionic units in an amount less than 50 mol %.

5. The process of claim 1, wherein the polybetaine (B) comprises homopolymers or copolymers comprising betaine units of formulae (-SPE-), (-SPP-), (-SHPE-) or (-SHPP-), and further wherein said polybetaine (B) has an absolute weight-average molar mass ranging from 10,000 g/mol to 150,000 g/mol.

6. The process of claim 1, wherein the polybetaine (B) is present in an amount sufficient to provide surface antideposition and/or antiadhesion properties with regard to soiling substances capable of being deposited on said surface.

7. The process of claim 1, wherein the polybetaine (B) is present in an amount ranging from 0.001 to 10% of the weight of said composition, and the at least one surface-active agent is present in an amount ranging from 0.005 to 60% of the weight of said composition.

8. The process of claim 1, wherein said composition further comprises: chelating agents, sequestering or scale-inhibiting agents, inorganic detergency adjuvants, bleaching agents, fillers, bleaching catalysts, agents that influence pH, polymers capable of controlling viscosity and/or foam stability, hydrotropic agents, hydrating agents, moisturizing agents, biocides, disinfectants, cleaning solvents, degreasing solvents, industrial cleaners, water-soluble organic solvents, cosolvents, antifoaming agents, abrasives, enzymes, fragrances, colorants or agents which inhibit the corrosion of metals.

9. The process of claim 1, wherein said composition has a pH of at least 7.5 and comprises from 0.001 to 5% by weight of polybetaine (B).

10. The process of claim 9, wherein said composition further comprises sequestering agents, scale-inhibiting agents, cationic biocides, disinfectants, surface-active agents, pH modifiers, water, cleaning organic solvents, degreasing organic solvents, co-solvents, water-soluble organic solvents, bleaching agents, or fragrances.

11. The process of claim 9, wherein said composition comprises:

from 0.001 to 1% by weight of polybetaine (B), from 1 to 10% by weight of a water-soluble solvent, from 1 to 5% by weight of a cleaning or degreasing solvent, from 0.1 to 2% by weight of monoethanolamine, from 0 to 5% by weight of at least one noncationic surface-active agent, and from 0 to 1% by weight of at least one disinfecting cationic surface-active agent, wherein the total amount of surface-active agent(s) ranges from 1 to 50% by weight, from 0 to 2% by weight of a dicarboxylic acid, from 0 to 5% of a bleaching agent, and from 70 to 98% by weight of water.

12. The process of claim 1, wherein said composition has a pH of less than 5 and comprises an inorganic or organic acid agent and from 0.001 to 5% of polybetaine (B) by weight of said composition.

13. The process of claim 12, wherein said composition further comprises nonionic, amphoteric, zwitterionic or anionic surface-active agents, cationic biocides or disinfectants, thickening agents, bleaching agents, water, solvents, fragrances or abrasives.

14. The process of claim 12, wherein said composition comprises:

from 0.05 to 5% by weight of polybetaine (B), from 0.1 to about 40% by weight of at least one acidic cleaning agent, from 0.5 to 10% by weight of at least one surface-active agent, optionally, from 0.1 to 2% by weight of at least one disinfecting cationic surface-active agent optionally from 0.1 to 3% by weight of at least one thickening agent, optionally, from 1 to 10% by weight of at least one bleaching agent, optionally, a preservative, a colorant, a fragrance or an abrasive, and from 50 to 95% by weight of water, wherein said composition has a pH ranging from 0.5 to 4.

15. The process of claim 1, wherein said composition comprises:

from 0.001 to 10% by weight of at least one polybetaine (B), from 0.005 to 20% by weight of at least one nonionic and/or anionic surface-active agent, from 0 to 10% by weight of at least one amphoteric surface-active agent, water, and from 0 to 30% by weight of at least one solvent, and wherein said composition has a pH ranging from 6 to 11.

16. The process of claim 1, wherein said composition comprises:

from 0.01 to 5% by weight of at least one polybetaine (B), from 0.2 to 10% by weight of at least one surface-active agent, optionally up to 90% by weight of at least one detergency adjuvant, up to 10% by weight of at least one auxiliary cleaning agent, up to 30% by weight of at least one bleaching agent, optionally combined with a bleaching activator, and up to 50% by weight of at least one filler, wherein said composition has a pH ranging from 8 to 13.

17. The process of claim 1, wherein said composition comprises:

from 0.02 to 10% by weight of at least one polybetaine (B), from 0.1 to 20% by weight of at least one surface-active agent, from 0 to 10% by weight of at least one calcium-sequestering organic acid, and from 0 to 15% by weight of at least one auxiliary detergency agent, and wherein said composition has a pH ranging from 4 to 7.

18. The process of claim 1, wherein said composition comprises:

from 0.1 to 10% by weight of at least one polybetaine (B), from 3 to 50% by weight of at least one surface-active agent, at least one non-cationic bactericide or disinfectant, at least one synthetic cationic polymer agent, at least one polymer capable of controlling viscosity and/or foam stability, at least one hydrotropic agent, and at least one hydrating or moisturizing agent or agent for protecting the skin, and wherein said composition has a pH ranging from 5 to 9.

19. The process of claim 1, wherein said composition comprises:

from 0.005 to 10% by weight of at least one polybetaine (B), from 0 to 30% by weight of at least one nonionic surface-active agent, from 0 to 30% by weight of at least one anionic surface-active agent, from 0 to 30% by weight of at least one amphoteric and/or zwitterionic surface-active agent, from 0 to 30% by weight of at least one cationic surface-active agent, from 0 to 99% by weight of at least one detergency adjuvant, optionally, hydrotropic agents, fillers or pH modifiers, wherein said composition has a pH ranging from 8 to 13.

20. The process of claim 1, wherein said composition comprises:

from 0.02 to 5% by weight of at least one polybetaine (B), from 0 to 30% by weight of at least one nonionic surface-active agent, from 0 to 30% by weight of at least one anionic surface-active agent, the total amount of surface-active agent being present in an amount ranging from 0.5 to 50% by weight, from 0 to 25% by weight of at least one detergency adjuvant, and from 0 to 2% by weight of a foam modifier, and wherein said composition has a pH ranging from 2 to 12.

21. The process of claim 1, wherein said composition comprises:

from 0.02 to 5% by weight of at least one polybetaine (B), from 0.5 to 5% by weight of at least one nonionic surface-active agent, water, optionally, at least one lower alcohol, and optionally, from 0.01 to 5% by weight of at least one metal-chelating agent, and wherein said composition has a pH ranging from 7 to 11.

22. The process of claim 1, wherein said composition comprises:

from 0.01 to 5% by weight of at least one polybetaine (B), from 0.1 to 1% by weight of at least one thickening agent, from 10 to 60% by weight of at least one abrasive agent, from 1 to 10% by weight of at least one nonionic surface-active agent, from 0 to 7% by weight of at least one solvent, and optionally, basifying or sequestering agents, and wherein said composition has a pH ranging from 7 to 12.

23. The process Of claim 1, wherein said composition comprises:

from 0.02 to 5% by weight of at least one polybetaine (B), from 1 to 50% by weight of at least one alkali metal salt, from 1 to 30% by weight of a mixture of surface-active agents, from 0 to 30% by weight of at least one solvent, wherein said composition has a pH ranging from 8 to 14.

24. The process of claim 1, wherein the polybetaine comprises homopolymers comprising betaine units (-SPE-).

25. The process of claim 1, wherein the polybetaine (B) has an absolute weight average molar mass ranging from 5,000 g/mol to 3,000,000 g/mol.

26. The process of claim 1, wherein the polybetaine (B) comprises a backbone comprising a polyalkylene chain interrupted by one or more nitrogen and/or sulfur atoms.

27. A process of preventing the redeposition or adhesion of soiling substances on a hard surface, comprising the step of:

treating said hard surface with a composition comprising in an aqueous or aqueous/alcoholic medium at least one surfactant and at least one polybetaine (B) comprising:

a homopolymer comprising betaine units comprising (-SPE-), (-SPP-), (-SHPE-), or (-SHPP-);

a copolymer comprising at least two different betaine units of formulae (-SPE-), (-SPP-), (-SHPE-) or (-SHPP-);

a copolymer comprising identical or different betaine units of formulae (-SPE-), (-SPP-), (-SHPE-) or (-SHPP-) and methacrylic acid units, wherein the amount of methacrylic acid units is less than 50 mol % of said copolymers; or mixtures thereof.

28. The process of claim 27, wherein the polybetaine (B) has an absolute weight average molar mass ranging from 5,000 g/mol to 3,000,000 g/mol.

* * * * *